US010450371B2

United States Patent
Clauss et al.

(10) Patent No.: US 10,450,371 B2
(45) Date of Patent: Oct. 22, 2019

(54) MONOCLONAL ANTIBODY AND ANTIGENS FOR DIAGNOSING AND TREATING LUNG DISEASE AND INJURY

(71) Applicant: Indiana University Research and Technology Corporation, Indianapolis, IN (US)

(72) Inventors: Matthias Clauss, Indianapolis, IN (US); Irina Petrache, Indianapolis, IN (US); Robert Voswinckel, Geissen (DE)

(73) Assignees: Indiana University Research and Technology Corporation, Indianapolis, IN (US); United States Government as represented by the Department of Veterans Affairs, Washington, DC (US)

(*) Notice: Subject to any disclaimer, the term of this patent is extended or adjusted under 35 U.S.C. 154(b) by 41 days.

(21) Appl. No.: 15/787,237

(22) Filed: Oct. 18, 2017

(65) Prior Publication Data

US 2018/0111987 A1    Apr. 26, 2018

Related U.S. Application Data

(62) Division of application No. 14/124,439, filed as application No. PCT/US2012/041722 on Jun. 8, 2012, now abandoned.

(60) Provisional application No. 61/494,720, filed on Jun. 8, 2011.

(51) Int. Cl.
| | |
|---|---|
| C12P 21/06 | (2006.01) |
| C12P 21/02 | (2006.01) |
| C12N 15/85 | (2006.01) |
| C07K 16/22 | (2006.01) |
| C07K 16/18 | (2006.01) |
| C07K 16/28 | (2006.01) |
| A61K 39/00 | (2006.01) |

(52) U.S. Cl.
CPC ............ *C07K 16/22* (2013.01); *C07K 16/18* (2013.01); *C07K 16/2866* (2013.01); *A61K 2039/505* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| 4,816,397 | A | 3/1989 | Boss et al. |
| 4,816,567 | A | 3/1989 | Cabilly et al. |
| 4,843,155 | A | 6/1989 | Chomczynski |
| 5,258,498 | A | 11/1993 | Huston et al. |
| 5,530,101 | A | 6/1996 | Queen et al. |
| 5,641,867 | A | 6/1997 | Stern et al. |
| 5,665,593 | A | 9/1997 | Kole et al. |
| 5,859,205 | A | 1/1999 | Adair et al. |
| 6,013,483 | A | 1/2000 | Coleman et al. |
| 8,486,405 | B2 | 7/2013 | Clauss et al. |
| 2002/0160957 | A1 | 10/2002 | Stern et al. |
| 2003/0039652 | A1 | 2/2003 | Schwarz |
| 2004/0110114 | A1 | 6/2004 | Zhang |
| 2010/0158883 | A1 | 6/2010 | Schimmel et al. |
| 2014/0221607 | A1 | 8/2014 | Clauss et al. |

FOREIGN PATENT DOCUMENTS

| WO | 0029620 A1 | 5/2000 |
| WO | 2008094012 A1 | 8/2008 |
| WO | 2009117680 A2 | 9/2009 |
| WO | 2010093214 A2 | 8/2010 |

OTHER PUBLICATIONS

Abaza MS, Atassi MZ. Effects of amino acid substitutions outside an antigenic site on protein binding to monoclonal antibodies of predetermined specificity obtained by peptide immunization: demonstration with region 94-100 (antigenic site 3) of myoglobin. J Protein Chem. Oct. 1992;11(5):433-44. (Year: 1992).*
Colman PM. Effects of amino acid sequence changes on antibody-antigen interactions. Res Immunol. 145(1):33-36, 1994. (Year: 1994).*
Li CH, Yamashiro D, Tseng LF, Chang WC, Ferrara P. beta-Endorphin omission analogs: dissociation of immunoreactivity from other biological activities. Proc Natl Acad Sci U S A. 77(6):3211-3214, 1980. (Year: 1980).*
Lederman S, et al. A single amino acid substitution in a common African allele of the CD4 molecule ablates binding of the monoclonal antibody, OKT4. Mol Immunol. 28(11):1171-81, 1991. (Year: 1991).*
Brown, et al., Tolerance to Single, But Not Multiple, Amino Acid Replacements in Antibody V(H) CDR2, Journal of Immunology, 1996, 156:3285-3291.
Cavarra, et al., Effects of Cigarette Smoke in Mice with Different Levels of a1-Proteinase Inhibitor and Sensitivity to Oxidants, Am. J. Respir. Crit. Care Med., 2001, 164:886-890.

(Continued)

*Primary Examiner* — Maher M Haddad
(74) *Attorney, Agent, or Firm* — Quarles & Brady LLP

(57) ABSTRACT

The present invention provides methods for diagnosing a patient with emphysema, COPD of lung injury caused by tobacco use by detecting the levels of EMAP II in a sample. Disclosed herein are the hypervariable regions for a rat monoclonal antibody that binds to a form of EMAP II. This disclosure also includes a polypeptide sequence included in EMAP II that is the target for the binding of the antibody to its target protein. This epitope serves as the basis for a humanized antibody that can be used to treat patients that suffer from pathologies that exhibit elevated levels of EMAP II expression.

4 Claims, 20 Drawing Sheets

Specification includes a Sequence Listing.

(56) References Cited

OTHER PUBLICATIONS

Clark, et al., FGF-10 Disrupts Lung Morphogenesis and Causes Pulmonary Adenomas In Vivo, Am. J. Physiol. Lung Cell Mol. Physiol., 2001, 280:L705-L715.

Clauss, et al., Lung Endothelial Monocyte-Activating Protein 2 is a Mediator of Cigarette Smoke-Induced Emphysema in Mice, Journal of Clinical Investigation, 2011, 121(6):2470-2479.

Kao, et al., Endothelial Monocyte-Activating Polypeptide II, Journal of Biological Chemistry, 1992, 267(28):20239-20247.

Kao, et al., A Peptide Derived from the Amino Terminus of Endothelial-Monocyte-Activating Polypeptide II Modulates Mononuclear and Polymorphonuclear Leukocyte Functions, Defines an Apparently Novel Cellular Interaction Site, and Induces an Acute Inflammatory Response, Journal of Biological Chemistry, 1994, 269(13):9774-9782.

Kao, et al., Characterization of a Novel Tumor-Derived Cytokine, Journal of Biological Chemistry, 1994, 269(40):25106-25119.

Knies, et al., Regulation of Endothelial Monocyte-Activating Polypeptide II Release by Apoptosis, Proc. Natl. Acad. Sci. USA, 1998, 95:12322-12327.

Knies, et al., Expression of EMAP II in the Developing and Adult Mouse, Apoptosis, 2000, 5(2):141-151.

Li, et al., Activation of the Signal Transducers and Activators of the Transcription 3 Pathway in Alveolar Epithelial Cells Induces Inflammation and Adenocarcinomas in Mouse Lung, Cancer Research, 2007, 67(18):8494-8503.

Padlan, Anatomy of the Antibody Molecule, Molecular Immunology, 1994, 31(3):169-217.

Parker, et al., MALDI/MS-Based Epitope Mapping of Antigens Bound to Immobilized Antibodies, Molecular Biotechnology, 2002, 20(1):49-62.

Paul, Fundamental Immunology, Third Edition, Raven Press, New York, 1993, pp. 292-295.

Petrache, et al., Ceramide Upregulation Causes Pulmonary Cell Apoptosis and Emphysema, Nat. Med., 2005, 11(5)491-498.

Petrache, et al., Superoxide Dismutase Protects Against Apoptosis and Alveolar Enlargement Induced by Ceramide, Am. J. Physiol. Lung Cell Mol. Physiol., 2008, 295:L44-L53.

Rajashekhar, et al., A Monoclonal Rat Anti-Mouse EMAP II Antibody that Functionally Neutralizes Pro- and Mature-EMAP II In Vitro, J. Immunol. Methods, 2009, 350(1-2):22-28.

Rudikoff, et al., Single Amino Acid Substitution Altering Antigen-Binding Specificity, Proc. Natl. Acad. Sci. USA, 1982, 79:1979-1983.

Shapiro, Vascular Atrophy and VEGFR-2 Signaling: Old Theories of Pulmonary Emphysema Meet New Data, Journal of Clinical Investigation, 2000, 106(11):1309-1310.

Sisson, et al., Expression of the Reverse Tetracycline-Transactivator Gene Causes Emphysema-Like Changes in Mice, Am. J. Respir. Cell Mol. Biol., 2006, 34:552-560.

Snider, et al., The Definition of Emphysema, Report of a National Heart, Lung, and Blood Institute, Division of Lung Diseases Workshop, American Review of Respiratory Disease, 1985, 132(1):182-185.

Tuder, et al., Apoptosis and Emphysema, Am. J. Respir. Cell Mol. Biol., 2003, 28:551-554.

Tuder, et al., Oxidative Stress and Apoptosis Interact and Cause Emphysema Due to Vascular Endothelial Growth Factor Receptor Blockade, Am. J. Respir. Cell Mol. Biol., 2003, 29:88-97.

Vajdos, et al., Comprehensive Functional Maps of the Antigen-Binding Site of an Anti-ErbB2 Antibody Obtained with Shotgun Scanning Mutagenesis, J. Mol. Biol., 2002, 320:415-428.

European Patent Office, Extended European Search Report, Application No. 12797368.3, dated Oct. 29, 2014, 15 pages.

PCT International Search Report, PCT/US2012/041722, dated Feb. 1, 2013, 3 pages.

* cited by examiner

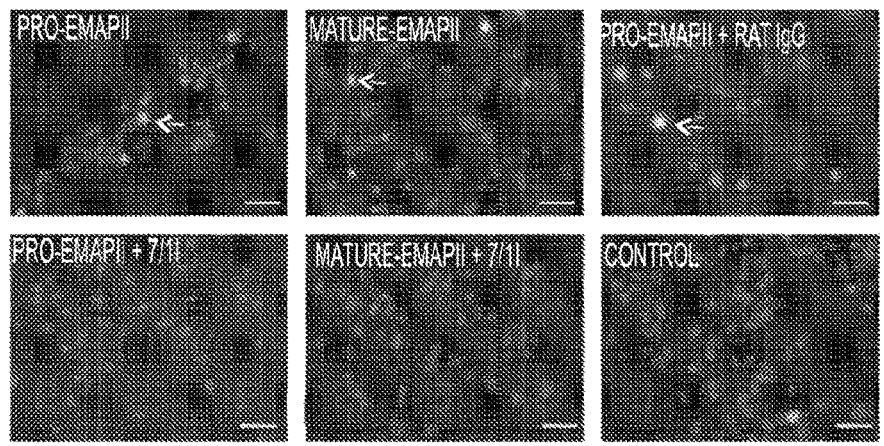
FIG. 11A
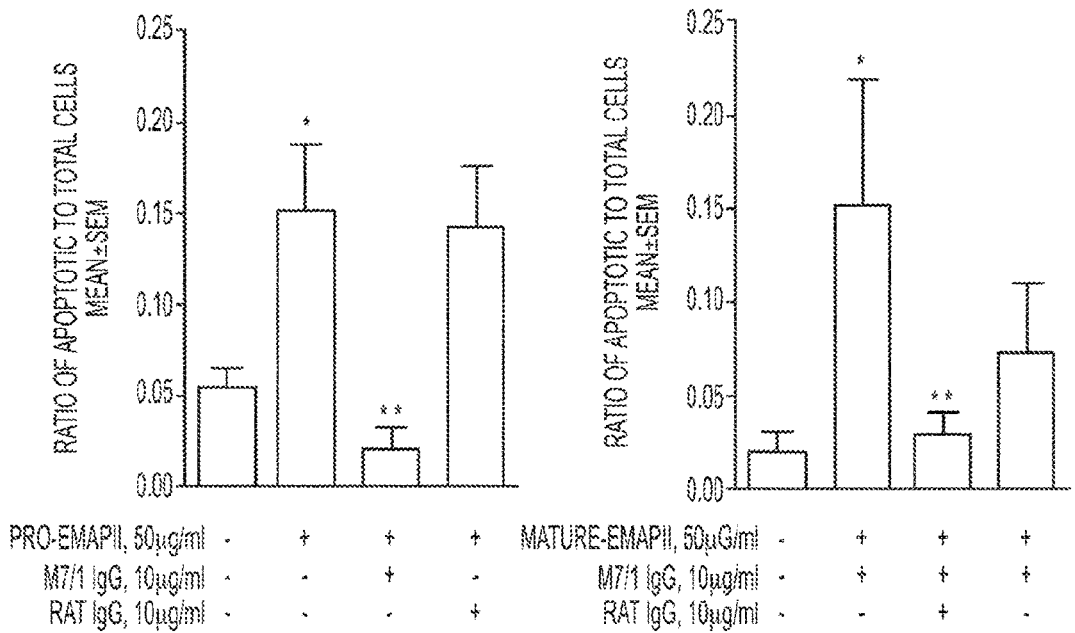
FIG. 11B
FIG. 11C

| TYPE | # | SEQUENCING RESULT SUMMARY |
|---|---|---|
| HEAVY CHAIN | H9 | NOT AN ANTIBODY GENE |
| HEAVY CHAIN | H11 | RAT HEAVY CHAIN |
| HEAVY CHAIN | H12 | RAT HEAVY CHAIN (IDENTICAL TO #H11) |
| LIGHT CHAIN | L2 | ABERRANT |
| LIGHT CHAIN | L4 | RAT LIGHT CHAIN |
| LIGHT CHAIN | L6 | RAT LIGHT CHAIN (IDENTICAL TO #L4) |
| LIGHT CHAIN | L9 | NOT AN ANTIBODY GENE |

Variable Region Sequences

VH

> MHC111H11.1

CDR Analysis (MHC111H11.1)

| | - CDR1 → | ← CDR2 → | ← CDR3 - |
|---|---|---|---|
| MHC111H11_1 | GFTFSDAA.... | IRTKPNNYAT | TSWSYDFDY |
| | (SEQ.ID.NO.5) | (SEQ.ID.NO.6) | (SEQ.ID.NO.7) |

Amino Acid Sequence in FASTA format (MHC111H11.1)
AVHLVESGGGFVQPTESLKISCAASGFTFSDAAMYWVRQAPGKGLEWVARIRTKPNNYATYYADSVKGRFTISRDDSKSM
VYLQMDNLKTEDTAMYYCTSWSYDFDYWGQGVMVTVSS
(SEQ. ID. NO. 2)

Nucleotide Sequence in FASTA format (MHC111H11.1)
GCGGTGCACCTTGTTGAGTCTGGTGGAGGATTTGTGCAGCCTACGGAGTCATTGAAAATCTCATGTGCAGCCTCTGGATT
CACCTTCAGTGATGCTGCCATGTACTGGGTCCGCCAGGCTCCAGGAAAGGGTCTGGAATGGGTTGCTCGCATAAGAACTA
AACCTAATAATTATGCAACATATTATGCTGATTCAGTGAAAGGCAGATTCACCATCTCCCGAGATGATTCAAAAAGCATG
GTCTACCTACAAATGGATAACTTGAAAACTGAGGACACAGCCATGTATTACTGTACATCATGGAGCTACGACTTTGATTA
CTGGGGCCAAGGAGTCATGGTCACAGTCTCCTCA
(SEQ. ID. NO. 1)

VL

> MHC111L4.3

CDR Analysis (MHC111L4.3)

| | - CDR1 → | ← CDR2 → | ← CDR3 - |
|---|---|---|---|
| MHC111L4_3 | KSLLHSSGKTY. | WMS....... | QQFLEYPLT |
| | (SEQ.ID.NO.8) | (SEQ.ID.NO.9) | (SEQ.ID.NO.10) |

Amino Acid Sequence in FASTA format (MHC111L4.3)
DIVMTQGALPNPVPSGESASITCQSSKSLLHSSGKTYLNWYLQRPGQSPHLLIYWMSTRASGVSDRLSGSGSGTDFTLKI
SSVEAEDVGVYYCQQFLEYPLTFGSGTKLEIK
(SEQ. ID. NO. 3)

Nucleotide Sequence in FASTA format (MHC111L4.3)
GATATTGTGATGACCCAGGGTGCACTCCCCAACCCTGTCCCCTCTGGAGAGTCAGCTTCCATCACCTGCCAGTCTAGTAA
GAGTCTGCTGCACAGCAGTGGCAAGACATACTTGAATTGGTATCTGCAGAGGCCAGGACAGTCTCCTCATCTCCTGATCT
ATTGGATGTCCACCCGTGCAATCAGGAGTCTCAGACAGGCTCACTGGCAGTGGGTCAGGAACAGATTTCACACTGAAAATC
AGCAGCGTGGAGGCTGAGGATGTGGGTGTGTATTACTGTCAGCAATTTCTAGAGTATCCTCTCACGTTCGGTTCTGGGAC
CAAGCTGGAGATCAAAC
(SEQ.ID.NO.4)

FIG. 15

```
1           20          30          40          50          60
MLPAVAVSEP  VVLRFMIFCR  LLAKMANNDA  VLKRLEQKGA  EADQIIEYLK  QQVSLLKEKA
70          80          90          100         110         120
ILQATLREEK  KLRVENAKLK  KETEELKQEL  IQAEIQNGVK  QIPFPSGTPL  HANSMVSENV
130         140         150         160         170     180
IQSTAVTTVS  SGTKEQIKGG  TGDEKKAKEK  IEKKGEKKEK  K QQSIAGSAD  SKPIDVSRLD
190         200         210         220         230     240
LRIGCIITAR  KHPDADSLIV  EEVDVGEIAP  RTVVSGLVNE  VPLEQMQNRM  VILCNLKPA
250         260         270         280         290         300
KMRGVLSQAN  VMCASSPEKI  EILAPPNGSV  PGDRITFDAF  PGEPDKELNP  KKKIWEQIQP
310         320         330         340
DLHTNDECVA  TYKGVPFEVK  GKGVCRAQIM  SNSGIK
```
⎫ (SEQ. ID. NO. 11)

(SEQ. ID. NO. 15)

FIG. 16

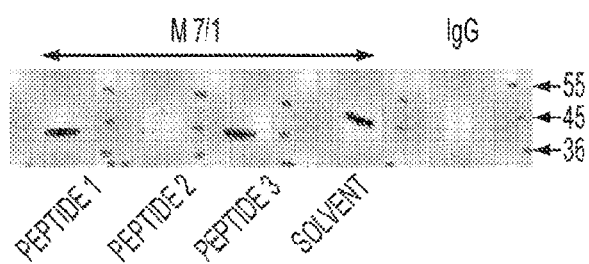

FIG. 17

MONOCLONAL ANTIBODY AND ANTIGENS FOR DIAGNOSING AND TREATING LUNG DISEASE AND INJURY

PRIORITY CLAIM

This application is a divisional of U.S. patent application Ser. No. 14/124,439, filed Apr. 18, 2014, which is a 371 U.S. National Phase entry of PCT/US2012/041722, filed Jun. 8, 2012, which claims the benefit of U.S. Provisional Patent Application No. 61/494,720, filed on Jun. 8, 2011, each of which is incorporated herein by reference in its entirety.

STATEMENT OF GOVERNMENT RIGHTS

This invention was made with government support under HL090950 awarded by National Institutes of Health. The government has certain rights in the invention.

FIELD

The present invention is directed generally to method for diagnosing and treating a patient with emphysema or chronic obstructive pulmonary disease (COPD), and more particularly to methods for diagnosing and treating a patient with emphysema or COPD by detecting the presence of endothelial monocyte activating protein II (EMAP II) and neutralizing EMAP II action.

BACKGROUND

Over 3.1 million Americans have been diagnosed with emphysema. Emphysema and chronic bronchitis are the two components of the syndrome of COPD. COPD is the fourth leading cause of death in America (See www.nhlbi.nih.gov/health/public/lung/other/copd_fact.htm#toc). This disease has no effective treatment that reverses its course or halts its progression.

Pulmonary emphysema is a prevalent fatal disease, characterized by loss of both matrix and cellular elements of the lung, thus impairing gas exchange between the alveolar space and the capillary blood. Emphysema is defined as "a condition of the lung characterized by abnormal, permanent enlargement of airspaces distal to the terminal bronchiole, accompanied by destruction of their walls, with or without obvious fibrosis". Report of a National Heart, Lung, and Blood Institute, Division of Lung Diseases workshop, *Am Rev Respir Dis* 132, 182-185. (1985). The concepts of permanent and destruction are critical in this definition as they convey the unique and characteristic distinguishing features of a disease process ultimately leading to the disappearance of lung tissue.

Although the environmental inducers in susceptible individuals have been identified, the mechanisms by which these initiate a loss of alveoli leading to emphysema are poorly understood. Over the past decades, inflammation and a protease/antiprotease imbalance have been proposed to act as downstream effectors of the lung destruction following chronic cigarette smoking, which accounts for most cases of emphysema. Pro-inflammatory stimuli are postulated to recruit and activate lung inflammatory cells, triggering matrix protease release and lung remodeling. Shapiro, S. D., *J Clin Invest* 106, 1309-1310 (2000). However, these models fail to fully account for the mechanisms behind the eradication of septal structures and the unique nature of lung destruction as compared to alterations seen in other inflammatory lung diseases. To account for the permanent destruction seen in emphysema, excessive apoptosis of structural alveolar cells have emerged as a second major mechanism of emphysema. Excessive alveolar endothelial apoptosis is thought to cause capillary regression, with subsequent loss of alveolar wall. Tuder, R. M. et al., *Am J Respir Cell Mol Biol* 28, 551-554 (2003). However, the coexistence of an excessive lung structural cell apoptosis with that of an activated inflammatory state in emphysema and the hierarchy of these two mechanisms have not yet been explained.

As can be seen, there is a need for a method for treating pulmonary emphysema. There is also a need for a method for diagnosing pulmonary emphysema in the early stages. Early diagnosis and subsequent treatment may result in more effective treatment of the disease and a better prognosis for the patient.

SUMMARY

In one aspect of the present invention there is provided a method of diagnosing a patient for emphysema or COPD comprising detecting the overexpression of EMAP II in a patient's biological sample where the sample may be serum, plasma, lung lavage or lung biopsy. The EMAP II may be detected by immunological methods such as enzyme-linked immunosorbent assay (ELISA), sandwich ELISA, Western blot, or mass spectrometry, for example. The overexpression of EMAP II may be determined by comparing to a control sample.

In another aspect of the present invention there is provided a method of predicting a patient's susceptibility of developing emphysema or COPD by detecting the presence of EMAP II in a patient's sample.

In a further aspect of the present invention there is provided a method for treating a patient having emphysema or COPD comprising administering a therapeutically effective amount of an EMAP II neutralizing compound. The EMAP II neutralizing compound may be an antibody, an agonist of the CXCR3 receptor, an siRNA or antisense RNA. The EMAP II neutralizing compound may be administered systemically or by inhalation.

Aspects of the invention include antibodies, either humanized or not-humanized, comprising: a heavy chain variable region, wherein said heavy chain variable region includes at least a portion of a first polypeptide according to SEQ. ID. NO. 2; and a light chain variable region, wherein said light chain variable region includes at least a portion of a second polypeptide according to SEQ. ID. NO. 3, wherein the antibodies bind to at least one form of EMAPII. In some embodiments the first polypeptide has at least 99 percent homology to SEQ. ID. NO. 2, and said second polypeptide has at least 99 percent homology to SEQ. ID. NO. 3. In other embodiments, the first polypeptide has at least 95 percent identity to SEQ. ID. NO. 2, and said second polypeptide has at least 95 percent identity to SEQ. ID. NO. 3. In other embodiments the first polypeptide has at least 99 percent identity to SEQ. ID. NO. 2, and said second polypeptide has at least 99 percent identity to SEQ. ID. NO. 3. And in still other embodiments, the first polypeptide is SEQ. ID. NO. 2, and said second polypeptide is SEQ. ID. NO. 3. In some embodiments the antibodies bind to at least the pro form of EMAPII (pro-EMAPII), and in some embodiments the antibodies bind to EMAPII found in humans and/or in mice and/or in other mammals.

Some aspects of the invention include antibodies, comprising: a heavy chain, wherein said heavy chain includes the heavy chain hypervariable regions CDR1, CDR2 and CDR3, wherein CDR1 includes at least a portion of the polypeptide according to SEQ. ID. NO. 5, CDR2 includes at least a portion of the polypeptide according to SEQ. ID. NO. 6, and CDR3 includes at least a portion of the polypeptide according to SEQ. ID. NO. 7; and a light chain, wherein said light chain includes the light chain hypervariable regions $CDR1_L$, $CDR2_L$, and $CDR3_L$, wherein $CDR1_L$ includes at least a portion of the polypeptide according to SEQ. ID. NO. 8, $CDR2_L$ includes at least a portion of the polypeptide according to SEQ. ID. NO. 9 and $CDR3_L$ includes at least a portion of the polypeptide according to SEQ. ID. NO. 10, wherein the heavy chain and the light chain form a portion of a humanized antibody, that binds to human EMAPII. In some embodiments, CDR1 is SEQ. ID. NO. 5, CDR2 is SEQ. ID. NO. 6, and CDR3 is SEQ. ID. NO. 7; and $CDR1_L$ is SEQ. ID. NO. 8, $CDR2_L$ is SEQ. ID. NO. 9, and $CDR3_L$ is SEQ. ID. NO. 10. In some embodiments the antibodies bind to at least the pro form of EMAPII (pro-EMAPII), and in some embodiments the antibodies bind to EMAPII found in humans and/or in mice and/or in other mammals. In some embodiments the antibodies are humanized.

Some aspects of the invention include epitopes, or other antigenic portions of EMAPII, that give rise to antibodies that bind to at least one form of mammalian EMAPII, comprising: an epitope of human EMAP II, wherein the epitope includes at least a portion of an isolated polypeptide according to SEQ. ID. NO. 12. In some embodiments, the isolated polypeptide has at least 95 percent homology to SEQ. ID. NO. 12. In still other embodiments, the isolated polypeptide has at least 99 percent homology to SEQ. ID. NO. 12. In yet other embodiments, the isolated polypeptide has at least 95 percent identity to SEQ. ID. NO. 12, while in some embodiments, the isolated polypeptide has at least 99 percent identity to SEQ. ID. NO. 12. In some embodiments, the isolated polypeptide is SEQ. ID. NO. 12. In some embodiments, the isolated polypeptide has at least 95 percent identity to SEQ. ID. NO. 11. In still other embodiments, the isolated polypeptide has at least 99 percent identity to SEQ. ID. NO. 11. In some embodiments, the isolated polypeptide is SEQ. ID. NO. 11. Some embodiments include these epitopes, or portions thereof, attached to at least one other polypeptide. Such co-joined polypeptides may not be naturally occurring, at least not in the organism that is expressing the polypeptide.

Some aspects of the invention include methods for making antibodies that bind to at least one form EMAPII found in either humans or in other mammals, these methods may comprise the steps of: producing a synthetic polypeptide wherein at least one portion of the synthetic polypeptide includes at least a portion of the polypeptide according to SEQ. ID. NO. 12. In some embodiments, the at least one portion of the synthetic polypeptide has at least 95 percent homology to SEQ. ID. NO. 12. In still other embodiments, that at least one portion of the synthetic polypeptide has at least 99 percent homology to SEQ. ID. NO. 12. In yet other embodiments, that at least one portion of the synthetic polypeptide has at least 95 percent identity to SEQ. ID. NO. 12. In some embodiments, the at least one portion of the synthetic polypeptide has at least 99 percent identity to SEQ. ID. NO. 12. In still other embodiments, the at least one portion of the synthetic polypeptide is SEQ. ID. NO. 12. In some embodiments, the at least one portion of the synthetic polypeptide has at least 95 percent homology to SEQ. ID. NO. 11. In other embodiments, the at least one portion of the synthetic polypeptide has at least 99 percent homology to SEQ. ID. NO. 11. In still other embodiments, the at least one portion of the synthetic polypeptide has at least 95 percent identity to SEQ. ID. NO. 11. In yet other embodiments, the at least one portion of the synthetic polypeptide has at least 99 percent identity to SEQ. ID. NO. 11. In some embodiments, at least one portion of the synthetic polypeptide is SEQ. ID. NO. 11. The inventive methods may include the step of contacting a synthetic polypeptide that includes at least one portion of at least one epitope of EMAPII disclosed herein with the immune system of a mammal. Some methods may include the further step of selecting a B-cell from said mammal contacted with said synthetic polypeptide, wherein said B-cell produces antibody that binds with high affinity to EMAPII. And in some embodiments, the antibodies raised to the epitopes disclose herein are humanized. In some embodiments, the humanized antibodies are used to treat a lung related disease or injury in humans and/or other mammals, or to diagnose such conditions in humans and/or other animals.

These and other features, aspects and advantages of the present invention will become better understood with reference to the following drawings, description and claims.

SEQUENCE LISTING

| | | |
|---|---|---|
| SEQ. ID. NO. 1 | GCGGTGCACCTTGTTGAGTCTGGTGGAGGATTTGT GCAGCCTACGGAGTCATTGAAAATCTCATGTGCA GCCTCTGGATTCACCTTCAGTGATGCTGCCATGTA CTGGGTCCGCCAGGCTCCAGGAAAGGGTCTGGAA TGGGTTGCTCGCATAAGAACTAAACCTAATAATT ATGCAACATATTATGCTGATTCAGTGAAAGGCAG ATTCACCATCTCCCGAGATGATTCAAAAAGCATG GTCTACCTACAAATGGATAACTTGAAAACTGAGG ACACAGCCATGTATTACTGTACATCATGGAGCTA CGACTTTGATTACTGGGGCCAAGGAGTCATGGTC ACAGTCTCCTCA | Nucleotide sequence of the IgG heavy chain from rat antibody hybridoma clone M7/1. |
| SEQ. ID. NO. 2 | AVHLVESGGGFVQPTESLKISCAASGFTFSDAAMY WVRQAPGKGLEWVARIRTKPNNYATYYADSVKGR FTISRDDSKSMVYLQMDNLKTEDTAMYYCTSWSY DFDYWGQGVMVTVSS | Polypeptide sequence of the IgG heavy chain from rat antibody hybridoma clone M7/1. |
| SEQ. ID. NO. 3 | DIVMTQGALPNPVPSGESASITCQSSKSLEHSSGKTY LNWYLQRPGQSPHLLIYWMSTRASGVSDRLSGSGS GTDFTLKISSVEAEDVGVYYCQQFLEYPLTFGSGTK LEIK | Polypeptide sequence of the IgG light chain from rat antibody hybridoma clone M7/1. |

-continued

| | SEQUENCE LISTING | |
|---|---|---|
| SEQ. ID. NO. 4 | GATATTGTGATGACCCAGGGTGCACTCCCCAACC CTGTCCCCTCTGGAGAGTCAGCTTCCATCACCTGC CAGTCTAGTAAGAGTCTGCTGCACAGCAGTGGCA AGACATACTTGAATTGGTATCTGCAGAGGCCAGG ACAGTCTCCTCATCTCCTGATCTATTGGATGTCCA CCCGTGCATCAGGAGTCTCAGACAGGCTCAGTGG CAGTGGGTCAGGAACAGATTTCACACTGAAAATC AGCAGCGTGGAGGCTGAGGATGTGGGTGTGTATT ACTGTCAGCAATTTCTAGAGTATCCTCTCACGTTC GGTTCTGGGACCAAGCTGGAGATCAAAC | Nucleotide sequence of the IgG light chain from rat antibody hybridoma clone M7/1. |
| SEQ. ID. NO. 5 | GFTFSDAA | Polypeptide CDR1 from IgG heavy chain of rat antibody hybridoma clone M7/1. |
| SEQ. ID. NO. 6 | IRTKPNNYAT | Polypeptide CDR2 from IgG heavy chain of rat antibody hybridoma clone M7/1. |
| SEQ. ID. NO. 7 | TSWSYDFDY | Polypeptide CDR3 from IgG heavy chain of rat antibody hybridoma clone M7/1. |
| SEQ. ID. NO. 8 | KSLLHSSGKTY | Polypeptide CDR1 from IgG light chain of rat antibody hybridoma clone M7/1. |
| SEQ. ID. NO. 9 | WMS | Polypeptide CDR2 from IgG light chain of rat antibody hybridoma clone M7/1. |
| SEQ. ID. NO. 10 | QQFLEYPLT | Polypeptide CDR3 from IgG light chain of rat antibody hybridoma clone M7/1. |
| SEQ. ID. NO. 11 | QQSIAGSADSKPIDVSRLDLRIGCIITARKHPDADSLY VEEVDVGEIAPRTVVSGLVNHVPLEQMQNRM | Polypeptide sequence identified in human EMAPII as the portion of the protein that is protected from trypsin digestion by the binding of rat antibody hybridoma clone M7/1. |
| SEQ. ID. NO. 12 | QQSIAGSADSKPIDVSR | Polypeptide sequence from human EMAPII that interacts with rat antibody hybridoma clone M7/1. |
| SEQ. ID. NO. 13 | KHPDADSLYVEEVDVGE | Polypeptide sequence from human EMAPII that does not appear to interact strongly with rat antibody hybridoma clone M7/1. |
| SEQ. ID. NO. 14 | VLKRLEQKGAEADQIIE | Random, synthetic polypeptide sequence that does not interact with rat antibody hybridoma clone M7/1. |

SEQUENCE LISTING

| SEQ. ID. NO. 15 | MLPAVAVSEPVVLRFMIFCRLLAKMANNDAVLKRL EQKGAEADQIIEYLKQQVSLLKEKAILQATLREEKK LRVENAKLKKEIEELKQELIQAEIQNGVKQIPFPSGT PLHANSMVSENVIQSTAVTTVSSGTKEQIKGGTGDE KKAKEKIEKKGEKKEKKQQSIAGSADSKPIDVSRLD LRIGCIITARKHPDADSLYVEEVDVGEIAPRTVVSGL VNHVPLEQMQNRMVILLCNLKPAKMRGVLSQAMV MCASSPEKIEILAPPNGSVPGDRITFDAFPGEPDKELN PKKKIWEQIQPDLHTNDECVATYKGVPFEVKGKGV CRAQTMSNSGIK | Polypeptide sequence of human EMAPII. |
|---|---|---|

BRIEF DESCRIPTION OF THE DRAWINGS

FIG. 11A. Fluorescent microscope images showing ihibition of EMAP II-induced apoptosis in endothelial cells with neutralizing antibody M 7/1 compared to control rat IgG.

FIG. 11B. A bar graph showing the ratio of apoptotic cells to total cells for pro-EMAPII with neutralizing antibody M 7/1 compared to control rat IgG.

FIG. 11C. A bar graph showing the ratio of apoptotic cells to total cells for mature EMAPII with neutralizing antibody M 7/1 compared to control rat IgG.

FIG. 15. Sequence data for the variable regions of the rat antibody.

FIG. 16. Scheme of EMAP II protein sequence. A range, which is protected from proteolytic degradation by binding to M7/1 antibody is highlighted.

FIG. 17. Binding competition of one peptide out of the protected area which is capable of competing with M7/1 antibody. Recombinant pro-EMAP II was submitted to Western blotting using control IgG and EMAP II neutralizing M7/1 antibody in the presence/absence of a 300 fold molar excess of peptide hexadecamers. Only Peptide 2 (QQSIAGSADSKPIDVSR) but not Peptide 1 (KHPDAD-SLYVEEVDVGE) or Peptide 3 (as a control) was able to compete with M7/1. Arrows indicate the position of molecular weight standards (in rel kDa).

DESCRIPTION

The following detailed description is of the best currently contemplated modes of carrying out the invention. The description is not to be taken in a limiting sense, but is made merely for the purpose of illustrating the general principles of the invention, since the scope of the invention is best defined by the appended claims. As used herein, unless explicitly stated otherwise or clearly implied otherwise, the term 'about' refers to a range of values plus or minus 10 percent, e.g. about 1.0 encompasses values from 0.9 to 1.1.

As used herein, unless explicitly stated otherwise or clearly implied otherwise, the terms 'therapeutically effective dose,' 'therapeutically effective amounts,' and the like, refer to a portion of a compound that has a net positive effect on the health and well being of a human or other animal. Therapeutic effects may include an improvement in longevity, quality of life and the like, and may also include a reduced susceptibility to developing disease or deteriorating health or well being. The effects may be immediate realized after a single dose and/or treatment or they may be cumulative and realized after a series of doses and/or treatments.

As used herein, unless explicitly stated otherwise or clearly implied otherwise, the term 'homology' as applied to polynucleotides refers to 3 nucleic acid long Condons that, while not identical to one another, encode the same information when transcribed into proteins. For a further discussion of this term as it is used in regards to polynucleotides, please see, Elliot and Elliot, *Biochemistry and Molecular Biology*, pages 293-295, published in 1997 by Oxford University Press, New York, N.Y., this portion of which is herby incorporated herein by reference in its entirety.

As used herein, unless explicitly stated otherwise or clearly implied otherwise, the term 'homology' as applied to polypeptides refers to amino acids commonly found in living organisms that are considered to be similar to one another in size, structure, and chemical reactivity. For a further discussion of this term as it is used in regards to polypeptides, please see, Stryer, L., *Biochemistry*, $2^{nd}$ edition, pages 13-17, copyright 1981, published by W. H. Freeman and Company, San Francisco, Calif., this portion of which is herby incorporated herein by reference in its entirety.

Figure 1:
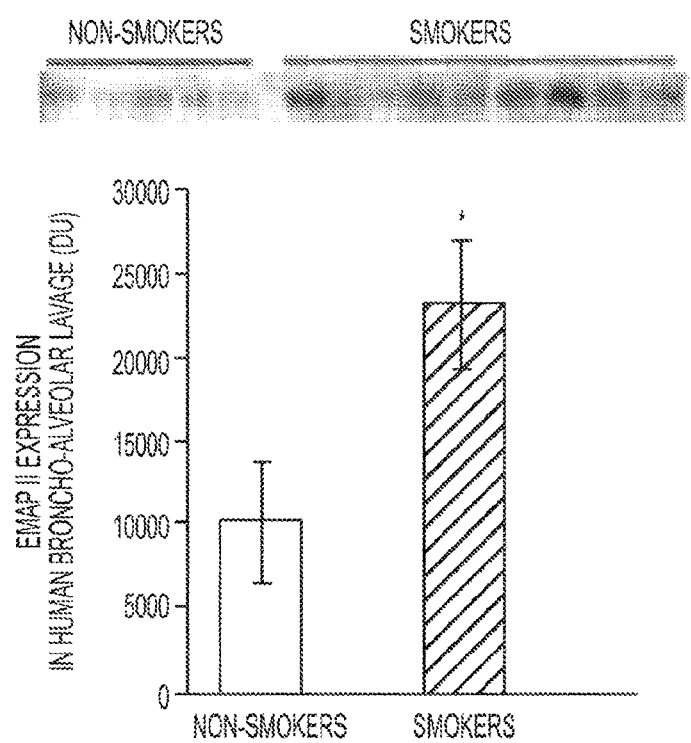
FIG. 1. A bar graph illustrating an increase in secreted EMAP II expression in humans in the broncho-alveolar lavage (BAL) of smokers compared to non-smokers.

Broadly, the present invention provides methods for diagnosing or treating a patient with emphysema or COPD comprising detecting the presence of EMAP II in a biological sample from a patient or treating with a therapeutically effective amount of an EMAP II neutralizing compound. The same method may also be used to determine if a patient is susceptible to developing emphysema or COPD. EMAP II is a cytokine induced by conditions present in emphysematous lungs including oxidative, apoptotic, and hypoxic cellular stresses. EMAP II is released from cells as either a 43 kD pro-form or a 23 kDa "mature" protein upon proteolytic cleavage by proteases including caspases and matrix metalloproteinases (MMPs), which are known to participate in COPD. Given the potent pro-apoptotic effect of EMAP II on lung endothelial cells, coupled with its ability to recruit pro-inflammatory monocytes, excessive EMAP II release in response to cigarette smoking may engage both lung endothelial cell apoptosis and accumulation of lung macrophages, and therefore may be a key molecular mediator of pulmonary emphysema. It has now been discovered by the inventors that smoke-induced emphysema is preceded by robust EMAP II production and apoptosis in mice and that lung-specific increases in EMAP II are sufficient to cause lung apoptosis and emphysema. Moreover, increased levels of EMAP II have now been measured in the lungs of emphysema patients and EMAP II has been found to be robustly upregulated in the BAL of smokers (FIG. 1). Therefore, EMAP II may be a biomarker for emphysema and COPD, allowing for earlier detection and treatment of these conditions.

In one embodiment a method is provided for diagnosing whether or not a patient has emphysema or COPD where the method may comprise the step of detecting EMAP II in a biological sample from a patient. It has been found that expression of EMAP II is significantly elevated by at least 2-fold in samples from patients who have emphysema or COPD. The method may further comprise comparing the EMAP II detected in the patient's sample with a control and diagnosing the patient as either having emphysema or COPD. The control may be a sample from a patient who does not have emphysema or COPD and, more specifically, from a patient who does not smoke. Control levels of EMAP II may be defined by a number of samples from control patients wherein the expression levels of EMAP II. It will be appreciated that the more control samples available, the better the comparison. The comparison may be a visual comparison observing elevated EMAP II levels or the amount of EMAP II in the sample and/or control may be quantified and then compared.

In one embodiment, the biological sample may be serum, plasma, BAL, or lung biopsy. Obtaining such samples is routine in the art. The overexpression of EMAP II in a biological sample may be assessed at the protein or nucleic acid level. In an illustrative embodiment, immunocytochemistry techniques are provided that utilize antibodies to detect the overexpression EMAP II in biological samples. In this aspect of the invention, at least one antibody directed to EMAP II may be used. Overexpression of EMAP II may also be detected by nucleic acid-based techniques, including, for example, hybridization and RT-PCR. Kits comprising reagents for practicing the methods of the invention are further provided.

Methods for detecting EMAP II may comprise any methods that determine the quantity or the presence of EMAP II either at the nucleic acid or protein level. Such methods are well known in the art and include but are not limited to Western blots, northern blots, southern blots, ELISA, immunoprecipitation, immunofluorescence, flow cytometry, immunocytochemistry, nucleic acid hybridization techniques, nucleic acid reverse transcription methods, and nucleic acid amplification methods. In illustrative embodiments, overexpression of EMAP II may be detected on a protein level using, for example, antibodies that are directed against specific biomarker proteins. The antibodies may be, but are not limited to, polyclonal and monoclonal antibodies. Examples of monoclonal antibodies are provided herein as well as in U.S. Pat. No. 5,641,867, which is incorporated by reference herein. These antibodies can be used in various methods such as Western blot, ELISA, immunoprecipitation, or immunocytochemistry techniques.

In one embodiment, EMAP II overexpression may be determined on the protein level. Antibodies specific for EMAP II may be utilized to detect the overexpression of a biomarker protein in a body sample. The method comprises obtaining a body sample from a patient, contacting the body sample with at least one antibody directed to EMAP II, and detecting antibody binding to determine if EMAP II is overexpressed in the patient sample. Overexpression of EMAP II may be determined by comparing the results to a control sample.

In an alternate embodiment, EMAP II overexpression may be detected at the nucleic acid level. Nucleic acid-based techniques for assessing expression are well known in the art and include, for example, determining the level of biomarker mRNA in a body sample. Many expression detection methods use isolated RNA. Any RNA isolation technique that does not select against the isolation of mRNA can be utilized for the purification of RNA from cervical cells (see, e.g., Ausubel et al., ed., Current Protocols in Molecular Biology, John Wiley & Sons, New York, 1987-1999). Additionally, large numbers of tissue samples can readily be processed using techniques well known to those of skill in the art, such as, for example, the single-step RNA isolation process of U.S. Pat. No. 4,843,155, which is incorporated by reference herein.

Isolated mRNA may be used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that can hybridize to the mRNA encoded by the gene being detected. The nucleic acid probe may be, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a biomarker of the present invention. The polynucleotide sequence of EMAP II is known in the art (i.e., U.S. Pat. No. 6,013,483, which is incorporated by reference herein), and nucleic acid probes may be selected without undue experimentation. Hybridization of an mRNA with the probe indicates that the biomarker in question is being expressed.

In another embodiment, methods are provided for determining a patient's susceptibility to developing emphysema or COPD. Although no symptoms may be present, those who smoke or were habitual smokers in the past have a significantly higher risk of developing emphysema than those who never smoked. Therefore, it may be desirable to determine the susceptibility of a patient who is a smoker to develop emphysema. Early detection may lead to a better treatment regime. The method may comprise the step of detecting EMAP II in a patient's sample as described above. The method may further comprise comparing the EMAP II in the patient's sample with a control as described above.

In yet another embodiment, kits for practicing the methods of the present invention are further provided. The kit may comprise at least one reagent (e.g., an antibody, a nucleic acid probe, etc.) for specifically detecting the expression of EMAP II. The kits may also comprise positive and/or negative controls to validate the activity and correct usage of reagents employed in accordance with the invention. Controls may include biological samples, such as lung tissue or lung lavage samples from control patients (negative control). EMAP II may be added to the control samples to provide positive controls.

In a further embodiment, methods are provided for treating a patient having emphysema or COPD comprising the step of administering a therapeutically effective amount of at least one EMAP II neutralizing compound. The neutralizing compound may be any compound or molecule that decreases or inhibits the activity or action of EMAP II in the patient. In one embodiment the neutralizing compound may be an anti-EMAP II antibody where the antibody may be a polyclonal or monoclonal antibody, antibody fragments, humanized or chimeric antibodies that retain the combining region that specifically binds to EMAP II.

In an alternate embodiment, the neutralizing compound may be an agonist of the CXCR3 receptor. The agonist may be a peptide, peptidomimetic or any other compound that disrupts the interaction between EMAP II and the CXCR3 receptor. In an illustrative embodiment, the neutralizing compound is an EMAP II analog. Interruption of the binding of EMAP II to CXCR3 may interfere with the detrimental action of EMAP II in lung tissue.

Figure 9:
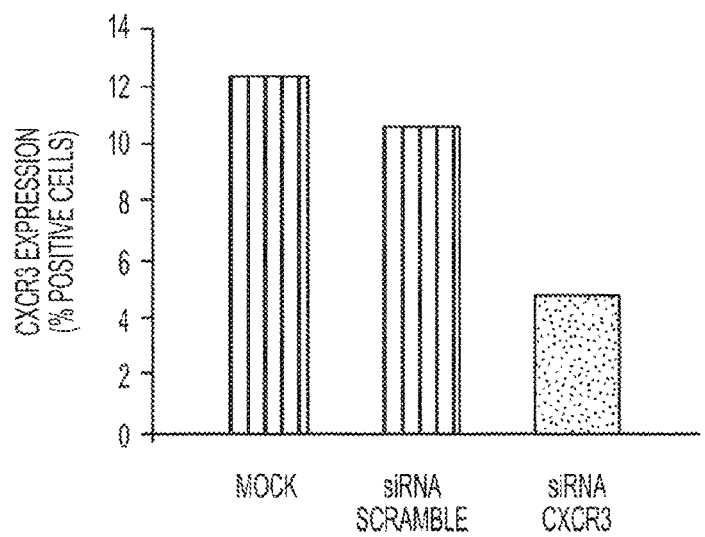
FIG. 9. A bar graph showing the effect of CXCR3-targeting siRNA on CXCR3 expression.

In yet another embodiment, the neutralizing compound may be a compound or molecule that decreases the expression of EMAP II. Non-limiting examples may be siRNA or antisense RNA targeted to EMAP II RNA or DNA. Alternatively, the neutralizing compound may be a compound or molecule such as, but not limited to, siRNA or antisense RNA, that interferes and decreases the expression of CXCR3. As shown in FIG. 9, when human lung microvascular endothelial cells were electroporated in the presence of CXCR3-targeting siRNA, CXCR3 expression levels showed reductions of about 60% to about 80%. As the nucleotide sequences are known for both EMAP II and CXCR3, one skilled in the art would be able to select siRNA and/or antisense RNA sequences for EMAP II and/or CXCR3 without undue experimentation. Examples of compounds and compositions for modulating the expression of EMAP II are disclosed in U.S. Patent Application Publication No. 2004/0110114 and U.S. Pat. No. 5,665,593, both of which are expressly incorporated by reference herein.

In one embodiment, protocols for the administration of the EMAP II neutralizing compounds are similar to the protocols for the administration of any other agent typically administered for a lung disorder. As a general guideline, protocols developed for the administration of any agent for the treatment of lung disease form a starting point for the administration of the EMAP II neutralizing compounds of the present invention. Thus, the EMAP II neutralizing compounds and compositions are administered via an inhalant or any other mechanism by which a disorder such as asthma is treated. In one embodiment of the invention, the active compounds or pharmaceutical formulations of the invention are administered directly to the lungs of the subject by any suitable means, but are preferably administered by administering an aerosol suspension of respirable particles comprised of the active compound, which the subject inhales. The active compound can be aerosolized in a variety of forms, such as, but not limited to, dry powder inhalants, metered dose inhalants, or liquid/liquid suspensions. The respirable particles may be liquid or solid. Alternatively, EMAP II neutralizing compounds may be administered systemically, either intravenously or through other means known in the art.

Any of the protocols, formulations, routes of administration and the like that have previously been used in the treatment of lung disorders may readily be modified for use in the present invention. In some cases, mechanical ventilation is appropriate. Such ventilation may include high-frequency oscillatory ventilation (HFOV) or other unconventional forms of mechanical ventilation. Theoretically, partial liquid ventilation (PLV) offers the advantage of lung lavage combined with ventilator support.

In another embodiment, the dosages are determined using an animal model, such as the EMAP II double transgenic models known to those of skill in the art, and modified and adapted to use in higher mammals. The total dose of therapeutic agent is administered in multiple doses or in a single dose. In certain embodiments, the compositions are administered alone, and in other embodiments the compositions are administered in conjunction with other therapeutics directed to the disease or directed to other symptoms thereof.

Regardless of the route of administration of the active compounds or formulations of the invention, the therapeutically effective dosage of any one active compound, the use of which is in the scope of present invention, will vary somewhat from compound to compound, and patient to patient, and will depend upon factors such as the age, weight and condition of the patient, and the route of delivery. Such dosages can be determined in accordance with routine pharmacological procedures known to those skilled in the art. In one exemplary embodiment, a dosage from about 0.1 to about 50 mg/kg will have therapeutic efficacy, with all weights being calculated based upon the weight of the active compound. Toxicity concerns at the higher level may restrict intravenous dosages to a lower level such as up to about 10 mg/kg. A dosage from about 10 mg/kg to about 50 mg/kg may be employed for oral administration. Typically, a dosage from about 0.5 mg/kg to 5 mg/kg may be employed for intramuscular injection. Preferred dosages are 1 µmol/kg to 50 µmol/kg, and more preferably 22 µmol/kg and 33 µmol/kg of the compound for intravenous or oral administration.

In another exemplary embodiment, dosages of the compounds of the present invention, for antisense oligonucleotides the dosage is preferably one which produces intracellular concentrations of the oligonucleotide of from 0.05 to 50 µM. Typically the dosage to a human will be from about 0.01, 0.1 or 1 mg/Kg up to 50, 100, or 150 mg/Kg. In an additional example, for antibodies the dosage is typically 0.01, 0.05 or 0.1 mg/Kg up to 20, 40 or 60 mg/Kg.

When administration of the active compounds or pharmaceutical formulations is via inhalation, the dosage of active compound will also vary depending on the condition being treated and the state of the subject, but generally may be an amount sufficient to achieve dissolved concentrations of active compound on the airway surfaces of the subject of from about $10^{-9}$ to about $10^{-1}$ Moles/liter, and more preferably from about $10^{-6}$ to about $10^{-4}$ Moles/liter.

Methods of formulating antibodies, peptides or other compounds for therapeutic administration are known to those of skill in the art. Methods of formulating siRNA or antisense RNA are also known in the art. Administration of these compositions according to the present invention will be via any common route so long as the target tissue is available via that route. Most commonly, these compositions are formulated for oral administration, such as by an inhalant. However, other conventional routes of administration (e.g., by subcutaneous, intravenous, intradermal, intramuscular, intramammary, intraperitoneal, intrathecal, intraocular, retrobulbar, intrapulmonary (e.g., term release), aerosol, sublingual, nasal, anal, vaginal, or transdermal delivery, or by surgical implantation at a particular site) are also used, particularly when oral administration is problematic. The treatment may consist of a single dose or a plurality of doses over a period of time.

It will be appreciated by those skilled in the art that the compounds of the present invention can be employed in a wide variety of pharmaceutical forms; the compound can be employed neat or admixed with a pharmaceutically acceptable carrier or other excipients or additives. Generally speaking, the compound will be administered orally or intravenously. It will be appreciated that therapeutically acceptable salts of the compounds of the present invention may also be employed. The selection of dosage, rate/frequency and means of administration is well within the skill of the artisan and may be left to the judgment of the treating physician. The method of the present invention may be employed alone or in conjunction with other therapeutic regimens.

Upon formulation, solutions will be administered in a manner compatible with the dosage formulation and in such amount as is therapeutically effective. The formulations are easily administered in a variety of dosage forms such as inhalents, injectable solutions, drug release capsules and the like. For parenteral administration in an aqueous solution, for example, the solution is suitably buffered if necessary and the liquid diluent first rendered isotonic with sufficient saline or glucose. These particular aqueous solutions are especially suitable for intravenous, intramuscular, subcutaneous and intraperitoneal administration.

The frequency of dosing will depend on the pharmacokinetic parameters of the agents and the routes of administration. The optimal pharmaceutical formulation will be determined by one of skill in the art depending on the route of administration and the desired dosage. Such formulations may influence the physical state, stability, rate of in vivo release and rate of in vivo clearance of the administered agents. Depending on the route of administration, a suitable dose is calculated according to body weight, body surface areas or organ size. The availability of animal models is particularly useful in facilitating a determination of appropriate dosages of a given therapeutic. Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

Typically, appropriate dosages are ascertained through the use of established assays for determining blood levels in conjunction with relevant dose response data. The final dosage regimen will be determined by the attending physician, considering factors which modify the action of drugs (e.g., the drug's specific activity, severity of the damage and the responsiveness of the patient, the age, condition, body-weight, sex and diet of the patient, the severity of any infection, time of administration and other clinical factors). As studies are conducted, further information will emerge regarding appropriate dosage levels and duration of treatment for specific diseases and conditions.

In one embodiment of the present invention methods are provided for monitoring the effectiveness of treatment of a patient for emphysema and/or COPD and undergoing treatment by determining the expression levels of EMAP II. The method may comprise the step of detecting EMAP II in a patient's sample as described above. The method may further comprise comparing the EMAP II in the patient's sample with a control as described above. Alternatively, the EMAP II expression levels may be compared to a sample from the same patient before treatment (i.e., from diagnosis) and/or samples from earlier in the treatment. In an illustrative embodiment, a method is provided comprising the steps of diagnosing a patient for emphysema and/or COPD by determining the expression level of EMAP II, treating the patient if the diagnosis was positive and monitoring the effectiveness of the treatment by determining the expression level of EMAP II during the treatment.

Example 1

Methods

Reagents and antibodies. All chemical reagents were purchased from Sigma-Aldrich (St. Louis, Mo.), unless otherwise stated. EMAP II antiserum was produced as recently described (Knies, U. E., Kroger, S., and Clauss, M. 2000. Expression of EMAP II in the developing and adult mouse. *Apoptosis* 5:141-151). Other antibodies employed were of commercial source, including MAC-3 (Becton Dickinson Biosciences, Franklin Lakes, N.J.), CXCR3 (R&D systems, Minneapolis, Minn.), and MMP-12 (R&D).

Cells. Human lung microvascular endothelial cells (HLMVEC) were obtained from Lonza (Allendale, N.J.) and maintained in culture medium consisting of EMB-2, 10% FBS, 0.4% hydrocortisone, 1.6% hFGF, 1% VEGF, 1% IGF-1, 1% ascorbic acid, 1% hEGF, 1% GA-100, and 1% heparin. All primary cell cultures were maintained at 37° C. in 5% $CO_2$ and 95% air. Experiments were performed up to passage 10 with cells at 80-100% confluence.

Monoclonal anti-EMAP II antibody. The rat monoclonal neutralizing antibody M7 against mouse EMAP II was developed by immunizing Lewis rats with recombinant murine pro-EMAP II. Lymphocytes isolated from the spleen and lymph nodes of immunized rats were fused with the mouse myeloma SP2/0, and Clones were selected by testing hybridoma supernatants in ELISA for binding both pro- and mature EMAP II. The clones most active in ELISA were further characterized by Western blotting and neutralization of EMAP II-induced endothelial apoptosis in tissue culture experiments (manuscript in preparation). For purification of MoAbs for in vivo studies, hybridomas were grown in protein-free hybridoma medium (GIBCO-BRL) and antibodies were purified with protein G-Sepharose (Pharmacia, Uppsala, Sweden).

Animal studies. C57/Bl6 mice were purchased from Jacksons Lab. A lung-specific inducible EMAP II transgenic mouse was generated by crossing the EMAP II responder mouse with homozygous transgenic mice containing the transactivator controlled by the lung epithelium specific CCSP. The EMAP II responder transgenic mouse contained the secreted (mature) form of EMAP II under a minimal promoter containing tetracycline-inducible sequences. Therefore the murine mature EMAP II cloned from meth mouse tumor cells (Knies, U. E., Behrensdorf, H. A., Mitchell, C. A., Deutsch, U., Risau, W., Drexler, H. C., and Clauss, M. 1998. Regulation of endothelial monocyte-activating polypeptide II release by apoptosis. *Proc Natl Acad Sci USA* 95:12322-12327) and fused to a signal peptide derived from INFb was inserted into the tet-repeat containing plasmid pUD10-3 by using Sac II and Xho I insertion sites. The resulting plasmid was injected into oocytes for implantation into foster mice and a transgenic line was established. After crossing of the resulting responder mice with the rtTA transactivator mice, the first generation of mice heterozygous for the EMAP II responder transgene were compared to the CCSP transactivator with CCSP transactivator-only transgenic mice. Of note, only the EMAP II/CCSP transactivator but not the CCSP transactivator-only transgene can induce EMAP II expression. With this design, CCSP transactivator background effects and tetracycline effects can be ruled out, as both groups can be treated with tetracycline. Transgenic mice were bred in an AAALAC accredited animal facility. Double transgenic EMAP II/CCSP-rtTA and single transgenic CCSP-rtTA mice were maintained on regular water until 3 to 4 month of age. Thereafter, the mice were placed on doxycycline treatment for up to 6 months. At the end of experiments, the mice were euthanized and the tissue was processed as described (Petrache, I., Natarajan, V., Zhen, L., Medler, T. R., Richter, A. T., Cho, C., Hubbard, W. C., Berdyshev, E. V., and Tuder, R. M. 2005. Ceramide upregulation causes pulmonary cell apoptosis and emphysema-like disease in mice. *Nat Med* 11:491-498). In addition, mice underwent BAL with 0.6 ml of PBS thrice. BAL cells were sedimented via centrifugation and the acellular fluid was then snap-frozen in liquid nitrogen and stored at −80° C. for further analysis.

Cigarette smoke exposure. Cigarette smoke exposure was performed as previously described (Cavarra, E., Bartalesi, B., Lucattelli, M., Fineschi, S., Lunghi, B., Gambelli, F., Ortiz, L. A., Martorana, P. A., and Lungarella, G. 2001. Effects of cigarette smoke in mice with different levels of alpha(1)-proteinase inhibitor and sensitivity to oxidants. *Am J Respir Crit Care Med* 164:886-890). Mice (C57/Bl6 mice, female, age 12 weeks; n=5-10 per group) were exposed to cigarette smoke or ambient air for up to 24 weeks. In a separate experiment, double transgenic EMAP II/CCSP transactivator or single transgenic CCSP transactivator control littermates, male and female, age 12 weeks; n=5-10 per group were exposed to cigarette smoke or ambient air by a similar protocol as above. Prior to (for the duration indicated) and during the cigarette smoke exposure, all transgenic mice received water with doxycycline. In a separate experiment, mice (DBA2, female, age 12 weeks; n=5-12 per group) were exposed to cigarette smoke as described above or ambient air for four months; during the third month of cigarette smoke exposure, two groups of mice exposed to cigarette smoke received either EMAP II antibody by nebulization or isotype IgG control, and one group exposed to ambient air received isotype IgG control. The day following the end of the cigarette smoking schedule in all experiments mice were euthanized and lung processing was performed as previously described (Petrache, I., Natarajan, V., Zhen, L., Medler, T. R., Richter, A. T., Cho, C., Hubbard, W. C., Berdyshev, E. V., and Tuder, R. M. 2005. Ceramide upregulation causes pulmonary cell apoptosis and emphysema-like disease in mice. *Nat Med* 11:491-498).

VEGF receptor blockade. VEGF receptor blockade was performed as previously described (Petrache, I., Natarajan, V., Zhen, L., Medler, T. R., Richter, A. T., Cho, C., Hubbard, W. C., Berdyshev, E. V., and Tuder, R. M. 2005. Ceramide upregulation causes pulmonary cell apoptosis and emphysema-like disease in mice. *Nat Med* 11:491-498). Mice (n=4-6/group) were injected with SU5416 (Calbiochem; 20 mg/kg, subcutaneously) or vehicle (carboxymethylcellulose) and the mice were euthanized at the indicated time.

Morphometric analysis was performed on coded slides as described, using a macro developed by R.M.T. for Metamorph (Tuder, R. M., Zhen, L., Cho, C. Y., Taraseviciene-Stewart, L., Kasahara, Y., Salvemini, D., Voelkel, N. F., and Flores, S. C. 2003. Oxidative stress and apoptosis interact and cause emphysema due to vascular endothelial growth factor receptor blockade. *Am J Respir Cell Mol Biol* 29:88-97; Aherne, W. A., and Dunnill, M. S. 1982. *Morphometry*. London: E. Arnold. xiv, 205 pp).

Human lung tissue. Human lung tissue consisted of sections from fixed, paraffin embedded explanted lung tissue from COPD patients and patients without lung disease (collected at the Johns Hopkins University). The specimen collection and storage were approved by the Institutional Research Board from the Johns Hopkins University.

Apoptosis was detected in lysates (Petrache, I., Natarajan, V., Zhen, L., Medler, T. R., Richter, A. T., Cho, C., Hubbard, W. C., Berdyshev, E. V., and Tuder, R. M. 2005. Ceramide upregulation causes pulmonary cell apoptosis and emphysema-like disease in mice. *Nat Med* 11:491-498) or inflated fixed lung sections enabling focus on alveoli, rather than large airways and vessels(Tuder, R. M., Zhen, L., Cho, C. Y., Taraseviciene-Stewart, L., Kasahara, Y., Salvemini, D., Voelkel, N. F., and Flores, S. C. 2003. Oxidative stress and apoptosis interact and cause emphysema due to vascular endothelial growth factor receptor blockade. *Am J Respir Cell Mol Biol* 29:88-97), via active caspase-3 IHC (Abcam and Cell Signaling) or in situ labeling of apoptotic DNA on murine lung, using rat serum as negative control. The immunostaining for both active casapase-3 and TUNEL was followed by DAPI (Molecular Probes) nuclear counterstaining. Executioner caspase (caspase-3 and/or -7) activity was measured with ApoONE Homogeneous Caspase-3/7 assay kit (Promega, Madison, Wis.). Human recombinant caspase-3 (Calbiochem) was utilized as positive control.

Lipid extraction and ceramide species measurement by tandem mass spectroscopy. Cellular or lung tissue lipids were extracted and lipid content was assessed by measurements of total lipid phosphorus ($P_i$) (Petrache, I., Natarajan, V., Zhen, L., Medler, T. R., Richter, A. T., Cho, C., Hubbard, W. C., Berdyshev, E. V., and Tuder, R. M. 2005. Ceramide upregulation causes pulmonary cell apoptosis and emphysema-like disease in mice. *Nat Med* 11:491-498). After lipid extraction, the following individual molecular species of ceramides were monitored: 14:0, 16:0, 18:0, 18:1, 20:0, 24:0, and 24:1-ceramides and utilizing $C_{17}$ ceramide as internal standard, ceramides were measured by combined liquid chromatography-tandem mass spectrometry (LC-MS/MS).

IHC. Paraffin sections were blocked with 10% rabbit (or goat serum if secondary antibody from goat) and incubated with antibodies or control antibodies. Polyclonal rabbit antiserum included EMAP II (1:500 dilute), capsase-3 (Cell signaling) and anti-MMP-12 (1:100, Sigma). Bound antibody was detected according to the manufacturer's instructions or a biotin-conjugated goat anti-rat IgG secondary antibody (Dianova, 1:100) and Streptavidin-coupled phycoerythrin (Dianova, 1:1000). For some application (anti-CD144, Pharmingen) cryosections were used. Sections were counterstained with DAPI and mounted with Mowiol 488 (Calbiochem). Microscopy was performed on either a Nicon Eclipse (TE200S) inverted fluorescent or a combined confocal/multi-photon (Spectraphysics laser, BioRad MRC1024MP) inverted system. Images and quantitative intensity (expression) data were processed by MetaMorph Imaging software (Universal).

Western blotting. Lung tissue was homogenized in RIPA buffer with protease inhibitors on ice and proteins were isolated by centrifugation at 10,000 g for 10 minutes at 4° C. BAL supernatants from transgenic mice or patients were collected and proteins were concentrated and precipitated by addition of trichloroacetic acid. Proteins were loaded in equal amounts (10 mg, unless otherwise noted) as determined by BCA protein concentration assay (Pierce, Rockville, Ill.). Total proteins were separated by SDS-PAGE using Novex gels (Invitrogen, Carlsbad, Calif.), followed by immunoblotting for EMAP II as previously described(Knies, U. E., Behrensdorf, H. A., Mitchell, C. A., Deutsch, U., Risau, W., Drexler, H. C., and Clauss, M. 1998. Regulation of endothelial monocyte-activating polypeptide II release by apoptosis. *Proc Natl Acad Sci USA* 95:12322-12327). Briefly, samples were mixed with Laemmli buffer, boiled at 95° C. for 10 min and loaded onto 15% SDS/PAGE gels. Proteins were separated by electrophoresis and blotted onto nitrocellulose (Pierce) using a semidry blotting apparatus. Unspecific binding was reduced by blocking the membrane in TBS/0.1% Tween 20/5% nonfat dry milk. The primary antibody (rabbit anti-EMAP II antiserum SA 2847, diluted 1:1000 in TBS/0.1% Tween 20/5% BSA) was applied overnight at 4° C. After washing, the membranes were incubated in a peroxidase-coupled goat anti-rabbit IgG (Dianova/Jackson Immuno Research; diluted 1:3500 in blocking buffer) for 1 h at room temperature and developed using an enhanced chemilluminescence kit (Amersham Pharmacia Biotech) Immunoblotting for EMAP II in lung lysates or BAL was performed by incubation with EMAP II-specific antibody (rabbit serum, produced as described above) in a 1:250 dilution in TBST for 1 h at room temperature. The chemilluminescent signals were quantified by densitometry (ImageQuant; Amersham, Piscataway, N.J.) and normalized by housekeeping proteins (actin, GAPDH, or vinculin).

Statistical analysis was performed with SigmaStat software using ANOVA with Student-Newman-Keuls post hoc test. Statistical difference was accepted at $p<0.05$.

Example 2

Effect of Cigarette Smoke Exposure or VEGF Receptor Inhibition on EMAP II Expression in the Mouse Lung To test the hypothesis that smoking induces cellular stress causing release of EMAP II, the effect of smoking on EMAP II protein production was measured. The extent of apoptosis induced by cigarette smoking in the mouse lung was also assessed. To more specifically address the correlation between endothelial cell death and EMAP II overproduction, the lung EMAP II expression in mice treated with a VEGF receptor blocker, which induces endothelial cell apoptosis was tested.

Mice susceptible to cigarette smoke-induced emphysema were exposed to cigarette smoke for various periods of time, from 4 days to 6 months. EMAP II expression was measured in lung lysates by Western blotting and apoptosis by caspase-3 activity and ceramide production. Finally, lungs from mice treated with VEGF receptor blocker SU5416 (20 mg/kg subcutaneously) were tested for EMAP II expression by Western blotting at 3 weeks, a time when lungs typically show morphometric changes of emphysema.

Figure 2A:
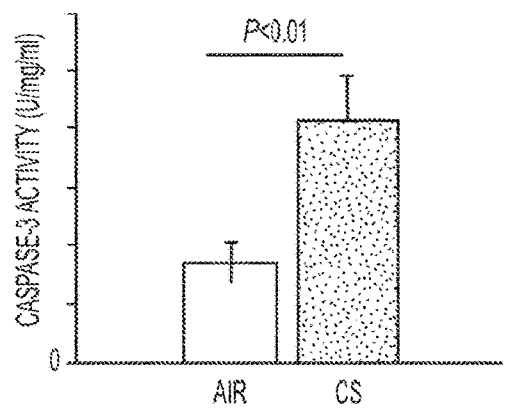
FIG. 2A. A bar graph showing the effect of cigarette smoke (CS) exposure on the activity levels of caspase-3 in mouse lungs.
Figure 2B:
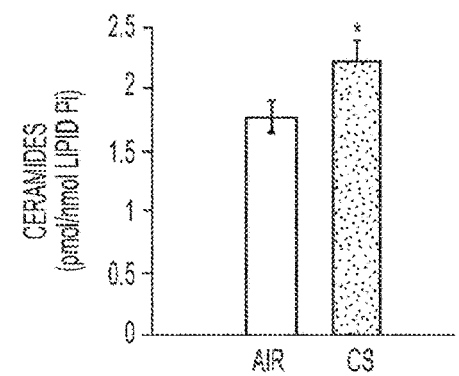
FIG. 2B. A bar graph showing the effect of cigarette smoke on the levels of pro-apoptotic ceramide levels in mouse lungs.
Figure 2C:
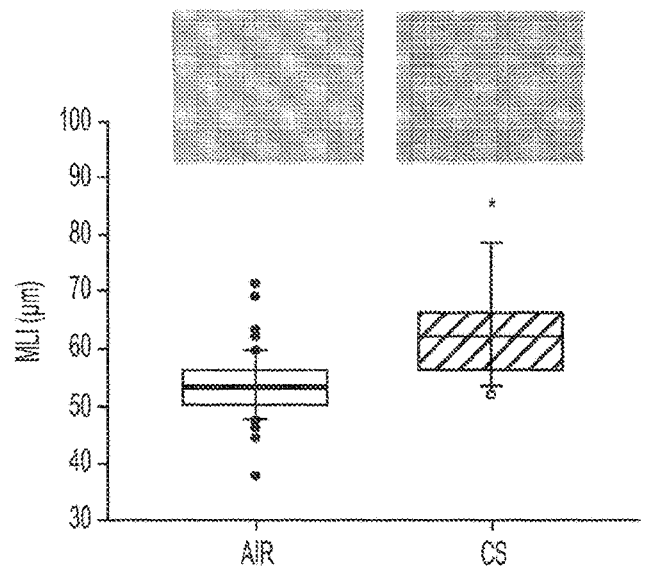
FIG. 2C. A bar graph of the alveolar size in mice exposed to cigarette smoke for 6 months.
Figure 3A:
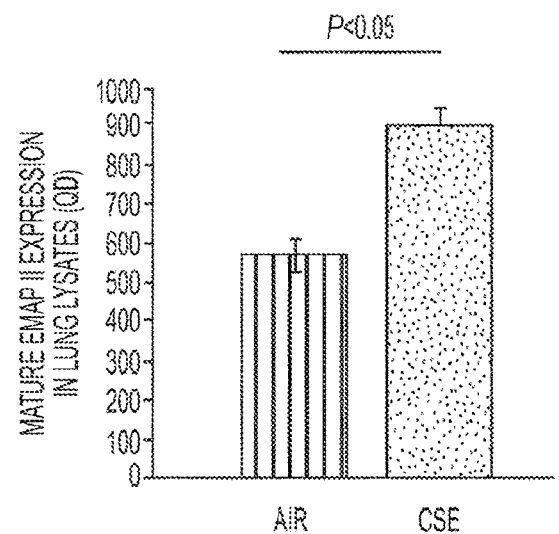
FIG. 3A. A bar graph that illustrates the effect of cigarette smoke exposure on the levels of EMAP II expression.
Figure 3B:
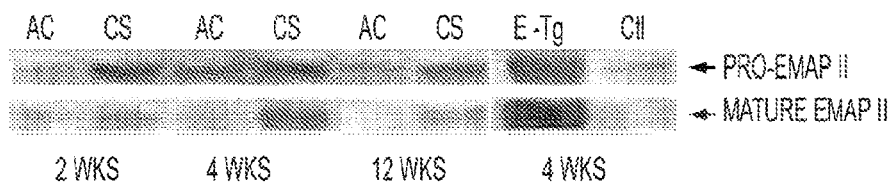
FIG. 3B. A Western blot showing the kinetics of EMAP II secretion in BAL from mice exposed to cigarette smoke (CS) or air (AC).
Figure 3C:
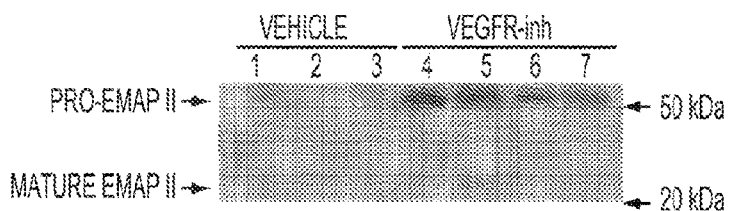
FIG. 3C. A Western blot showing VEGF receptor inhibition with SU5416.

Cigarette smoke CS exposure for 4 days increased caspase-3 activity in lungs, and thus increased apoptotic activity as early as 1 week after cigarette smoke exposure in C57/Bl6 mice (FIG. 2A), long preceding the increases in airspaces typical of emphysema that occurred at 6 months of cigarette smoke exposure (FIG. 2C). At 1 month the lung content of ceramide increased in DBA 2 mice (FIG. 2B). These early increases in apoptotic activity were paralleled by an increase in both the pro- and mature forms of EMAP II expression (FIGS. 3A and 3B). Similarly, in another experimental model of apoptosis-dependent emphysema, SU5416 induced a robust EMAP II expression at 4 weeks in the C57/Bl6 mouse lung (FIG. 3C).

These results suggest an increase in apoptotic rates and EMAP II production in the emphysematous lungs of mice, including those exposed to cigarette smoke. While not wishing to be bound by theory, the increase in EMAP II may result from direct cell stress, or from apoptosis-activated caspases. Furthermore, EMAP II release may itself be responsible for inducing further lung endothelial cell apoptosis.

Example 3

Effect of Elevated Lung EMAP II Levels on the Severity of Cigarette Smoke-induced Injury in the Mouse Lung To test whether increases in EMAP II have an additive or a synergistic effect with cigarette smoking in the lung, EMAP II expression in the lungs was induced for 8 weeks prior to cigarette smoke exposure. The conditional transgenic overexpression system is presented in more detail in Example 4.

An increase in baseline EMAP II levels in the lung followed by a 4 week cigarette smoke exposure profoundly elevated the levels of mature EMAP II and increased the number of inflammatory cells in the inter-alveolar/interstitial tissue consistent with a further increase in parenchymal inflammation compared to smoking alone.

These results suggest that EMAP II contributes to cigarette smoke-induced lung injury and may independently worsen or predispose the lung to a more severe inflammatory response to smoke.

Example 4

Transgenic Induction of EMAP II in the Lung Causes Emphysema-Like Disease in Mice To study the mechanism by which increased lung levels of EMAP II trigger emphysema, a transgenic murine model of inducible expression of EMAP II in the lung was established using the tetracycline inducible transactivator (TTA) controlled by the lung epithelium-specific CCSP promoter. Although both EMAP II forms were available as inducible constructs, the mature EMAP II was initially assessed since it has been classically involved in the apoptosis and inflammatory effects of EMAP II. Furthermore, the pro-EMAP II is usually easily cleaved to generate mature EMAP II, making it difficult to assess its specific, mature-form-independent effects.

The transgenic mouse tet EMAP II (responder mouse) contained the mature form of EMAP II under a minimal promoter containing tetracycline-inducible sequences. This mouse line does not express elevated levels of EMAP II because it lacks the transactivator gene product. The responder mouse was crossed with homozygous transgenic mice containing the transactivator controlled by the lung epithelium specific CCSP promoter (CCSP mouse line), which in this form targets gene expression predominately in alveolar type II cells versus in Clara cells. Clark, J. C., et al. *Am J Physiol Lung Cell Mol Physiol* 280, L705-715 (2001); Li, Y., et al. *Cancer Res* 67, 8494-8503 (2007). The first generation of mice heterozygous for the EMAP II responder transgene and the CCSP transactivator with CCSP transactivator-only transgenic mice were compared. Of note, this CCSP transactivator-only transgene cannot induce EMAP II overexpression. With this design, CCSP transactivator background effects as described recently (Sisson, T. H., et al. *Am J Respir Cell Mol Biol* 34, 552-560 (2006)) and tetracycline effects can be ruled out, as both groups were treated with tetracycline. Furthermore, the tetracycline concentration used in this induction system is insufficient to ameliorate any inflammation and MMP activities. Expression was analyzed by Western of BAL and lung lysates and by IHC of lung sections using EMAP II antiserum. To determine whether long term EMAP II over-expression in the lung induces an emphysema-like phenotype, double transgenic mice with tetracycline in the drinking water were treated for up to 6 months.

Figure 4A:
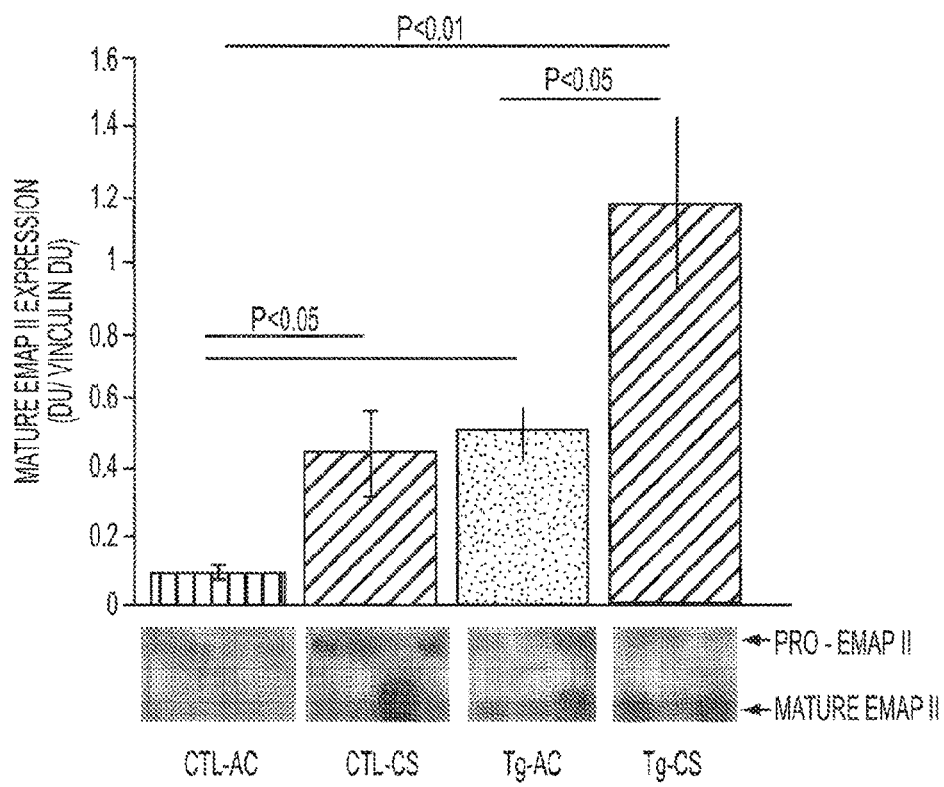
FIG. 4A. A bar graph and Western blot that illustrates the effect of cigarette smoke exposure on EMAP II levels in lung lysates.
Figure 4B:
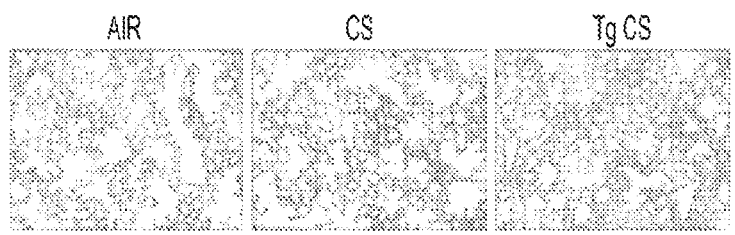
FIG. 4B. Photomicrographs that show the effect of cigarette smoke exposure on the amount of inflammatory cells in lung tissue.
Figure 5A:
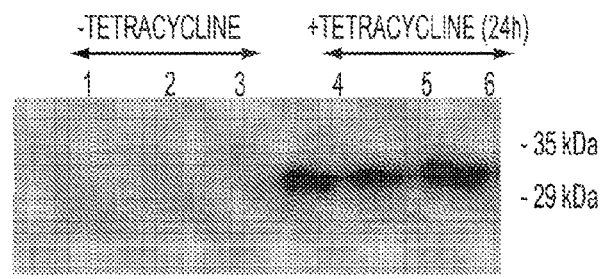
FIG. 5A. A Western blot showing the induction of EMAP II in mice after 24 hours of tetracycline treatment.
Figure 7A:
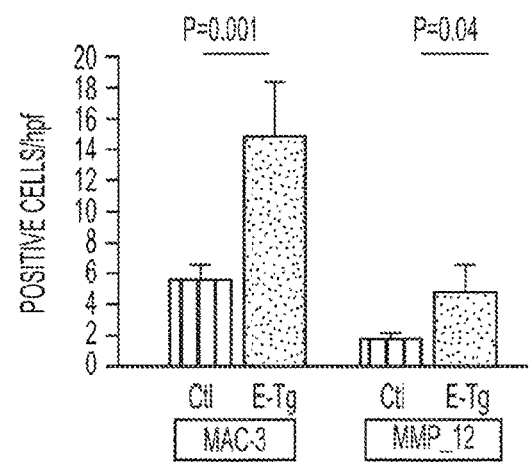
FIG. 7A. A bar graph showing the number of cells in the lungs of mice overexpressing EMAP II compared to a control.

Transgenic induction of EMAP II caused high EMAP II secretion into the lungs of double transgenic mice after as early as 24 h (FIGS. 3B, 4B and 5A). Of note, the EMAP II expression pattern in the lung parenchyma resembled typical staining pattern for alveolar type II cells, which is in line with the reported selectivity for this transgenic promoter. EMAP II double transgenic mice treated for 3 or 6 months with tetracycline to induce EMAP II expression displayed significant emphysema-like increase in airspace (FIG. 7A). This was measured both by the mean linear intercept and the recently established method of volume-weighted mean airspace volume. Morphological parameters for emphysema appear to increase proportional to the duration of EMAP II induction, which is reflected by morphometry: the volume-weighted mean airspace volume was 1.36E+08±0.15, n=5 in control mice; 1.56E+08±0.3 in EMAP II transgenic mice induced for 3 months; and 1.91E+08±0.3, n=6, in those induced for 6 months; p=0.027)

Increased EMAP II production in the lungs leads to formation of emphysema-like morphological changes. This is the first evidence that excessive levels of a protein causing endothelial cell death leads to emphysema.

Example 5

Excessive EMAP II Production in the Lung Causes Pulmonary Cell Apoptosis

To address the hypothesis that EMAP II over-production promotes emphysema via endothelial cell apoptosis, apoptosis in the lungs of EMAP II-overexpressing mice was assessed. To determine the EMAP II-specificity of apoptosis, and to test in vivo the efficacy of an EMAP II-neutralizing antibody, the anti-EMAP antibody was administered to a group of EMAP II transgenic animals.

Fluorescent microscopy with specific active caspase-3 antibody of lung sections from EMAP II/CCSP double transgenic (EMAP II tg) or CCSP control transgenic animals (ctl) was used to detect the presence and localization of apoptosis in the lung. Anti-VE-cadherin antibody was used to test for colocalization of apoptosis with endothelial cells.

In addition, lung lysates were tested for caspase-3 activity by fluorimetric enzymatic assay (Promega). For the neutralization experiment, EMAP II tg (induced for 48 h before harvesting the lungs) received anti-EMAP II rat monoclonal antibody or isotype IgG control, by a single injection i.p., 12 h after the induction.

Figure 6A:
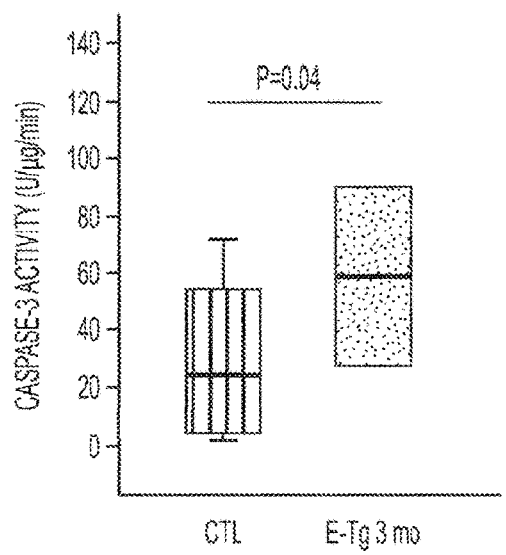
FIG. 6A. A graph showing the caspase-3 activity in lung lysates of single or EMAP II double transgenic mice after 3 months.
Figure 6B:
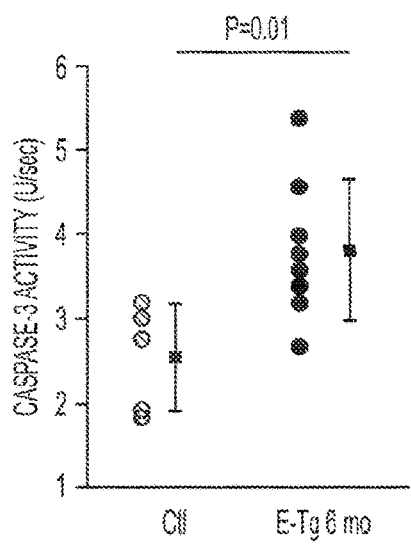
FIG. 6B. A graph showing caspase-3 activity in lung lysates from single or EMAP II double transgenic mice after 6 months.
Figure 6C:
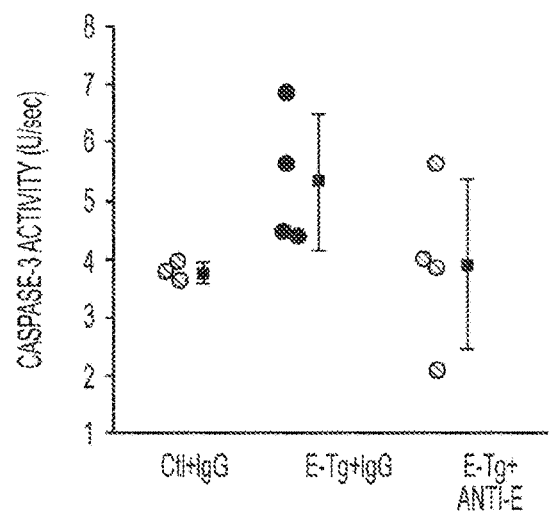
FIG. 6C. A graph showing caspase-3 activity in lungs of single or EMAP II double transgenic mice treated with nonspecific control IgG and neutralizing EMAP II antibody.

EMAP II significantly increased the number of caspase-3 positive cells in the lung parenchyma of EMAP II tg versus ctl (~6 fold, p=0.003, by fluorescence quantitation using Metamorph on blinded slides) as early as 3 weeks after induction. The increased lung apoptosis persisted after 3 months and 6 months of EMAP II inductions as assessed by both IHC and caspase-3 activity from lung lysates (FIGS. 6A and 6B). The majority of caspase-3 positive cells were endothelial cells. There was a trend for decreased apoptosis in mice receiving neutralizing EMAP II antibody (FIG. 6C).

It is thought that changes by in situ detection of activated caspase-3 were more dramatically significant due to the higher signal to noise ratio in lysates resulting from having many other non-dying cells other than endothelial cells. Finally, although not yet statistically significant, the neutralizing effects of anti-EMAP II antibody are extremely encouraging in that apoptosis observed is EMAP II dependent and that the neutralizing antibody is effective in vivo. Taken together these data support the conclusion that endothelial cell apoptosis may be a key event in EMAP II-induced emphysema formation.

Example 6

Effect of Lung-specific EMAP II Overexpression on the Monocyte Recruitment in the Lung It was previously shown that EMAP II attracted and activated monocytes in a dose-dependent manner, caused inflammation when locally injected, and triggered leukostasis in the lung upon systemic application. Kao, J., et al., *J Biol Chem* 269, 25106-25119 (1994); Kao, J., et al., *J Biol Chem* 269, 9774-9782 (1994). The chemotactic effect of EMAP II on monocytes may be important in the inflammatory responses associated with emphysema.

Confocal imaging of fluorescent immunostaining of markers for lung macrophage accumulation and activation in lung sections from EMAP II/CCSP double transgenic vs. CCSP single transgenic animals was performed using MAC-3-(macrophage marker) as well as TNFα-, MMP-9-, and MMP-12-specific antibodies.

Figure 7B:
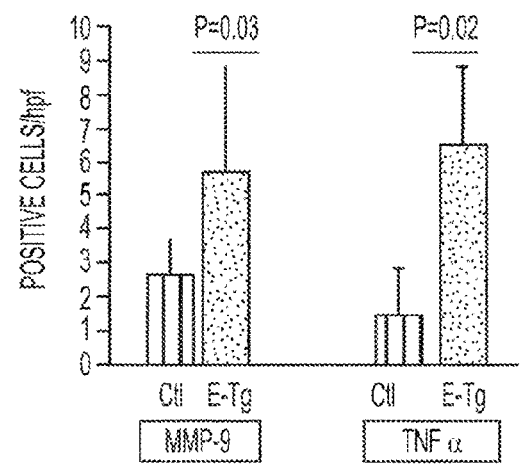
FIG. 7B. A bar graph showing the quantification MMP-9 and TNFα-positive cells.

The lung specific overexpression of mature EMAP II dramatically increased the numbers of MAC-3-expressing cells along with staining for TNFα-, MMP-9, MMP-12 in the lung (FIGS. 7A and 7B). The vast majority of TNFα-, MMP-9, MMP-12 and MAC-3 positive cells displayed a large nuclear phenotype, characteristic for macrophages, whereas MMP-12-positivity colocalized not only with Mac-3 (FIG. 7A), but also with other cells within the alveolar wall, possibly epithelial cells.

The increase in Mac-3 positive cells was most likely due to recruitment of monocytes form the circulation to the lung, as the proliferation capacity of already resident lung macrophages is extremely low. These macrophages may be a source of inflammatory activation in the lungs of EMAP II transgenic.

Example 7

Both Pro- and Mature EMAP 11-Induce Significant Apoptosis in Human Primary Microvascular Lung Endothelial Cells Situations associated with stress can induce both forms of EMAP II. It is not known which form is more potent in inducing endothelial cell apoptosis and whether the mechanism by which this occurs is form-dependent. These detailed mechanistic assays can only be done in cell cultures. However to increase their significance, only primary lung microvascular endothelial cells of human origin, commercially obtained (Lonza) were tested.

Figure 8A:
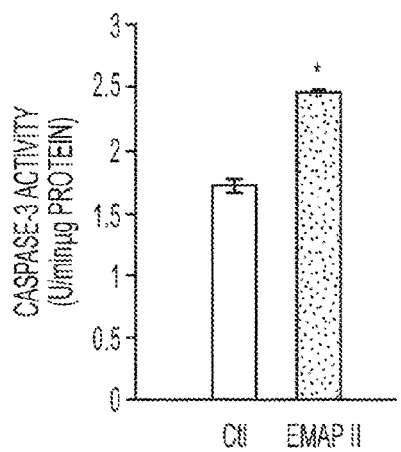
FIG. 8A. A bar graph showing the effect of EMAP II overexpression on caspase-3 activity.
Figure 8B:
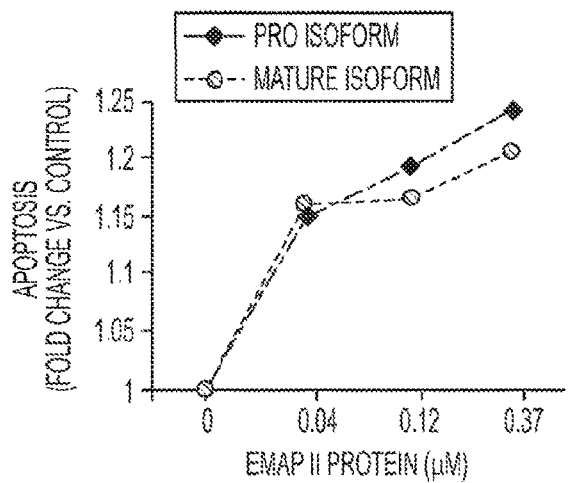
FIG. 8B. A graph showing the effect of treatment of lung microvascular endothleial cells with recombinant proteins comprising the pro- and mature isoforms of EMAP II on apoptosis.
Figure 8C:
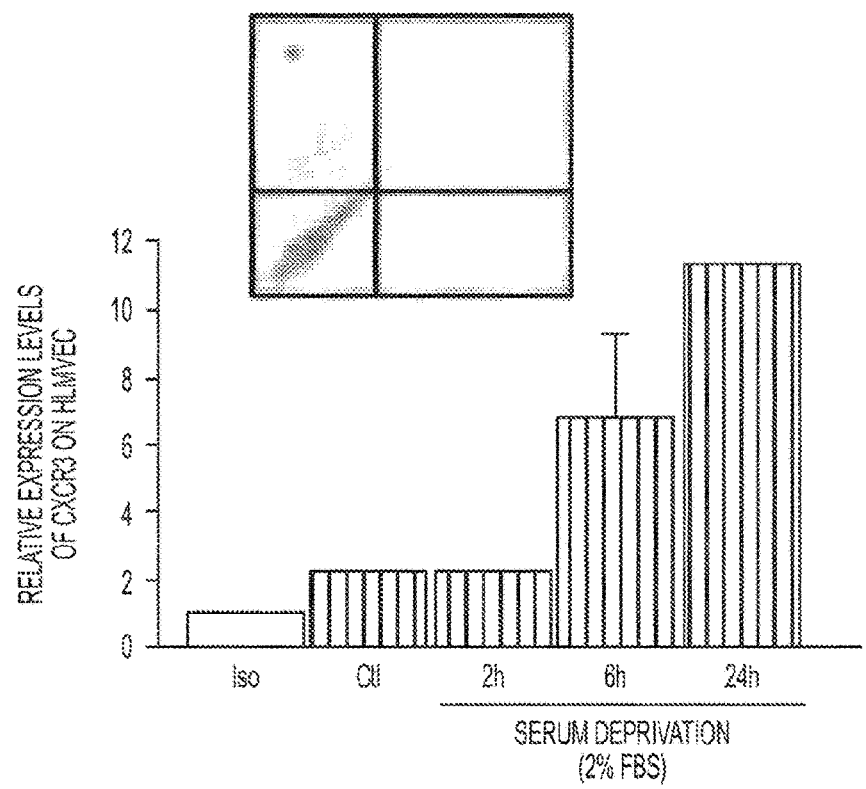
FIG. 8C. A bar graph showing the expression levels of CXCR3 in cells cultured with low serum.
Figure 8D:
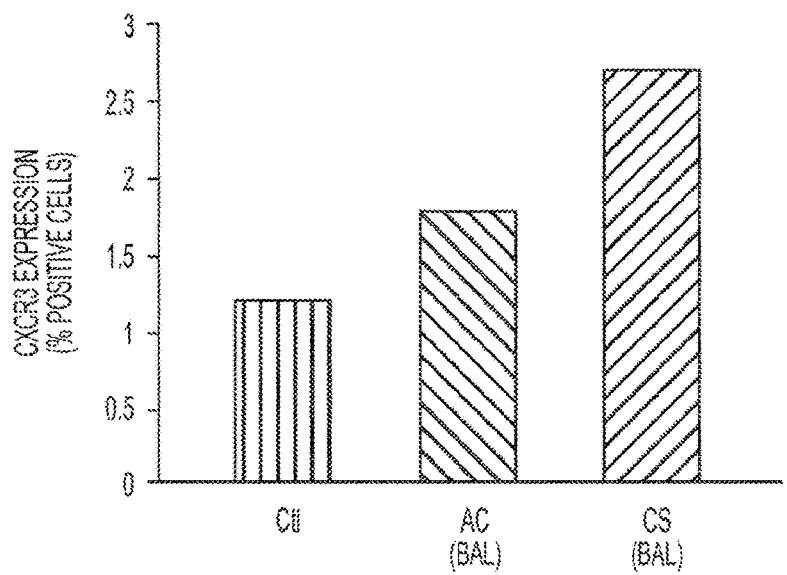
FIG. 8D. A bar graph showing the expression levels of CXCR3 in cells treated with acellular BAL from mice exposed to cigarette smoke (CS) or air (AC).
Figure 8E:
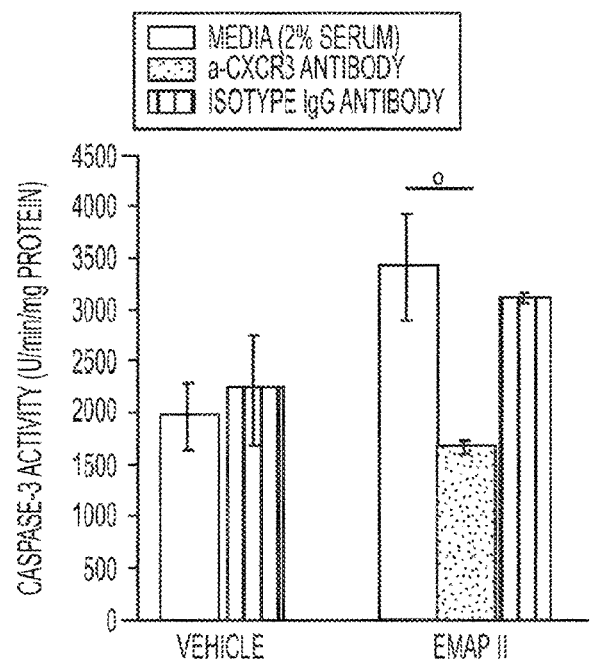
FIG. 8E. A bar graph showing the effect of anti-CXCR3 antibody on caspase-3 activity.

Primary human lung microvascular endothelial cells were treated with recombinant pro- or mature-EMAP II at 10-16 µg/ml. Apoptosis was measured by caspase-3 activity and Annexin/PI staining by flow cytometry. Treatment with both forms of EMAP II resulted in increased apoptosis as measured by caspase-3 activity (FIG. 8A) and Annexin/PI staining (FIG. 8E).

Both the pro- and mature EMAP II forms appeared equally potent at inducing endothelial cell apoptosis in culture conditions.

Example 8

The Stress-sensitive CXCR3 Receptor Mediates EMAP 11-Induced Lung Endothelial Cell Apoptosis To investigate whether the CXCR3 receptor mediates EMAP II-induced lung endothelial cell apoptosis, its expression on primary human lung microvascular endothelial cells was initially assessed and secondly, its function was inhibited by specific blocking antibodies.

Primary human lung microvascular endothelial cells were cultured in normal growth media, as well as in media containing low serum concentration (2%), or even treated with acellular BAL from smoked or control mice. The BAL was concentrated (50-fold) and cells were incubated with a volume representing 10% of the original undiluted cellular BAL. CXCR3 was detected by using labeled anti-CXCR3 antibody detected by FACS. To assess the role of the CXCR3 caspase-3 activation in lung microvascular endothelial cells, cells with blocking anti-CXCR3 antibodies were pretreated (1 µg/ml, pretreated for 30 min).

Primary human lung microvascular endothelial cells express CXCR3 at low levels. Stressful conditions such as serum starvation, treatment with BAL from smoked but not from non-smoked mice, or even electroporation (FIG. 9) increased significantly its expression (FIGS. 8A-8D). Anti-CXCR3 antibodies, but not isotype IgG antibodies significantly reduced mature EMAP II-induced endothelial cell death (FIGS. 8A-8D).

These results are strong evidence that EMAP II-induced endothelial cell apoptosis in the lung may be mediated primarily by the CXCR3 receptor. This implies that CXCR3 mediates the functional effects of EMAP II on both endothelial cells and monocytes and may be important for the development of cigarette smoke emphysema.

Example 9

Figure 10A:
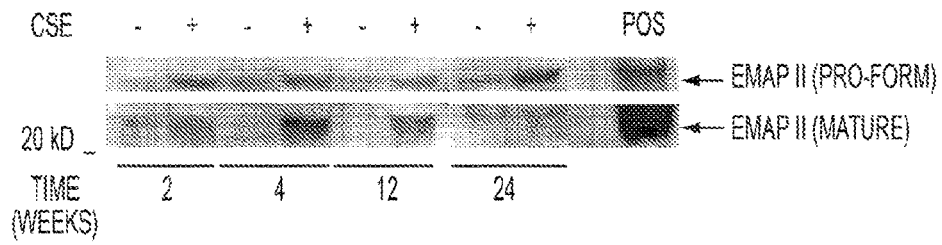
FIG. 10A. An immunoblot showing the effect of cigarette smoke exposure on EMAP II expression in the mouse lung.
Figure 10B:
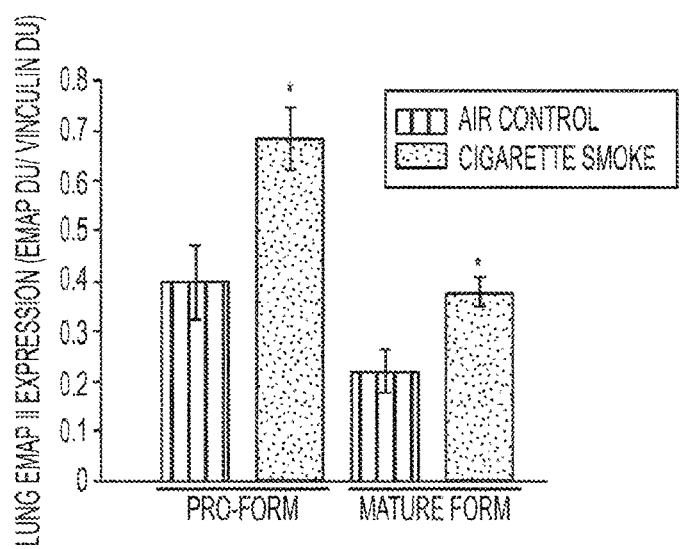
FIG. 10B. A bar graph showing EMAP II expression in the lung parenchyma of DBA2 mice exposed to cigarette smoke for 4 weeks.

Cigarette Smoke Increased the Expression of Both EMAP II Forms in the Mouse Lung Based on previous findings that mature EMAP II is released by apoptosis and the proform upon stress, the induction of EMAP II in the lung in vivo upon exposure to cigarette smoke was investigated. Therefore, EMAP II expression was measured in two inbred mouse strains, C57/Bl6 and DBA2, which reportedly develop emphysema after chronic exposure to cigarette smoke for 6 or 4 months, respectively. Cigarette smoke exposure (CSE) (for up to 24 weeks) profoundly increased both the pro- and mature forms of EMAP II (approximately 8- and 2-fold, respectively) secreted in the BAL and detected by Western blotting (FIG. 10A). Equal volume (100 μl) of acellular BAL from each mouse was pooled (n=5 per time point), then equally concentrated (10×) and equally loaded (10 μl) in each lane. Specific EMAP II antibody (1:250) detected both the pro- and the mature forms of the EMAP II in the lavage. BAL from the EMAP II overexpressing transgenic (Tg) mice was utilized as positive (Pos) control. Similar increases in the two forms of EMAP II expression were noted in the lung parenchyma of DBA2 mice exposed to cigarette smoke for 4 weeks (FIG. 10B).

Figure 10C:
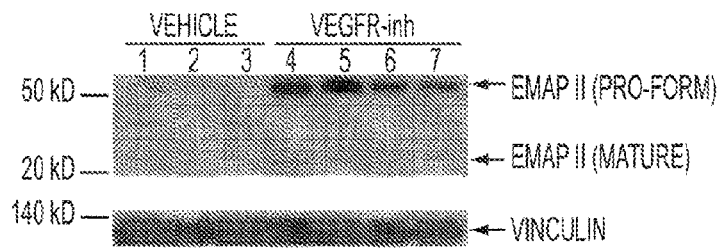
FIG. 10C. An immunoblot showing lung EMAP II expression in a mouse model of apoptosis-dependent emphysema.
Figure 10D:
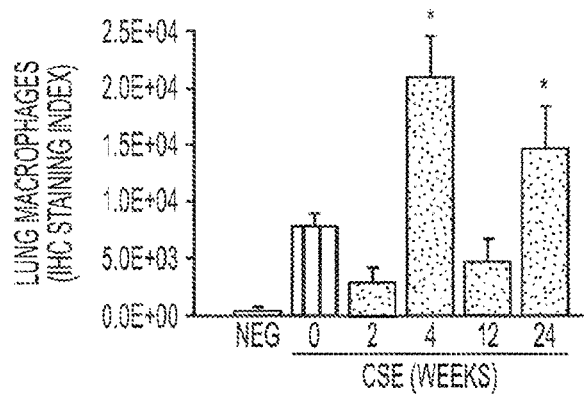
FIG. 10D. A bar graph showing lung macrophage accumulation in pulmonary parenchyma in response to cigarette smoke exposure.
Figure 10E:
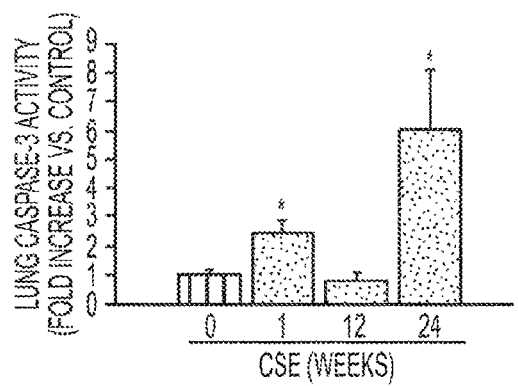
FIG. 10E. A bar graph showing lung apoptosis as measured by capsase-3 activity assay in lung lysates following cigarette smoke exposure.

Interestingly, in a distinct experimental model of apoptosis-dependent murine emphysema which develops secondary to VEGF receptor inhibition, EMAP II expression was also markedly upregulated in the lungs of mice which developed airspace enlargement compared to control mice, but predominantly in the pro-form (FIG. 10C). FIG. 10C shows EMAP II expression in the lung parenchyma of C57/Bl6 mice at four weeks after treatment with the VEGF receptor inhibitor (VEGFR-inh). Each lane was loaded with 40 μg lung lysate from individual mice treated with vehicle (carboxymethyl cellulose) or the VEGFR-inh SU5416 (20 mg/kg, subcutaneous). Vinculin was immunoblotted as loading control. The kinetics of EMAP II elevation in response to cigarette smoking demonstrated that the increase in lung EMAP II secretion preceded that of alveolar macrophage accumulation, first noted at 4 weeks, but not 2 weeks of cigarette smoke exposure (FIG. 10D). The kinetic relationship of the EMAP II increase with the caspase-3 activation in the lung was more complex, as significant caspase-3 activation was noted throughout the time course of the EMAP II increases in response to cigarette smoking in mice (FIG. 10E). Since EMAP II's biological properties include monocyte chemoattraction and apoptosis of proliferative and hypoxic endothelial cells, EMAP II could play an important role in the inflammatory and apoptotic responses in the lung in response to cigarette smoke exposure.

Example 10

Neutralization of Pro and Mature-EMAP 11-Induced Endothelial Cell Apoptosis

Because mature EMAP II has been shown to induce endothelial apoptosis, it was investigated whether a rat antibody hybridoma clone M7/1 (M/71 antibody) was also able to neutralize apoptosis induced by EMAP II. In particular it was investigated whether this M7/1 antibody was able to neutralize pro-apoptotic activities of both pro- and mature EMAP II.

EMAP II induced apoptosis was assessed by quantification of TUNEL-positive cells (FIG. 11A). Endothelial cells incubated with pro-EMAPII protein (50 μg/ml) or mature-EMAPII protein (50 μg/ml) demonstrated a significant apoptosis (arrows) as shown by TUNEL (*p<0.01). Pretreatment of these cells with the neutralizing M 7/1 antibody (10 μg/ml), but not with control rat IgG, significantly (**p<0.03) inhibited apoptosis induced by both pro and mature EMAPII as shown from representative fluorescent microscope images following TUNEL assay. Quantification of TUNEL positive cells by MetaMorph software normalized to total DAPI nuclear positive cells is also shown for pro-EMAPII (FIG. 11B) and mature EMAPII (FIG. 11C). Data shown are from a representative experiment performed in triplicates and repeated independently two additional times with similar results. Scale bar=50 μm.

Thus, EMAP II induced apoptosis was significantly (p<0.03) blocked by the anti-EMAP II M 7/1 antibody, but not by control rat IgG (FIGS. 11A-11C). Interestingly, it was observed that pro-EMAP II at the same molar concentrations as mature EMAP II was also a strong inducer of endothelial apoptosis. Again, the M 7/1 antibody was able to completely neutralize this activity (p<0.01). These data demonstrate that the M7/1 antibody can effectively neutralize the pro-apoptotic function of both EMAP II forms and may be a suitable tool to inhibit pathophysiological activities of this protein in mice. (Rajashekhar, G. et al, A monoclonal rat anti-mouse EMAP II antibody that functionally neutralizes pro- and mature-EMAP II in vitro, *J Immunol Methods*. 2009 Oct. 31; 350(1-2): 22-28).

Example 11

Figure 12A:
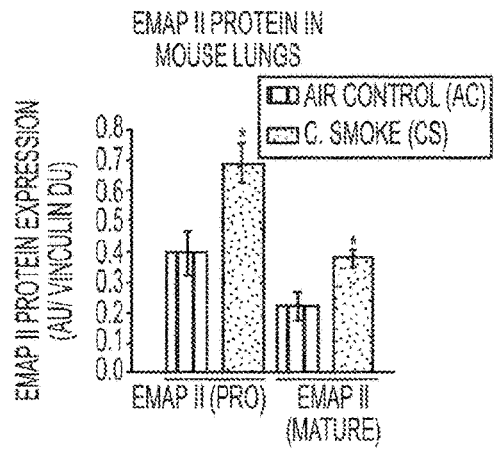
FIG. 12A. Graph of EMAPII (pro and mature forms) in lung lysates from mice exposed to Cigarette Smoke (CS) for 4 weeks compared with EMAPII levels in the lungs of mice that were not exposed to CS (ambient air control group, AC); EMAPII levels were assessed by Western blots (mean densitometry units [DUs] normalized to vinculin±SEM; *P<0.05 versus control; n=5/group).

Neutralization of EMAPII Levels Markedly Reduces CS-Induced Lungemphysema in Mice Because EMAPII has been shown to be produced and released by apoptosis, hypoxia, and cellular stress, it was investigated whether EMAPII is induced in the lung in vivo upon exposure to cigarette smoke (CS). EMAPII protein expression was measured in the DBA/2 mouse strain, which develops emphysema after chronic exposure to CS as early 16 weeks, exhibiting a 20% increase in airspace size, compared with only a 9% increase measured in the C57BL/6 strain at this time point, respectively. CS exposure for only 4 weeks significantly increased the pro and mature forms of EMAPII expression in the lung parenchyma of DBA/2 mice compared with that in control mice exposed to ambient air (air control [AC]), measured by immunoblotting (FIG. 12A).

Figure 12B:
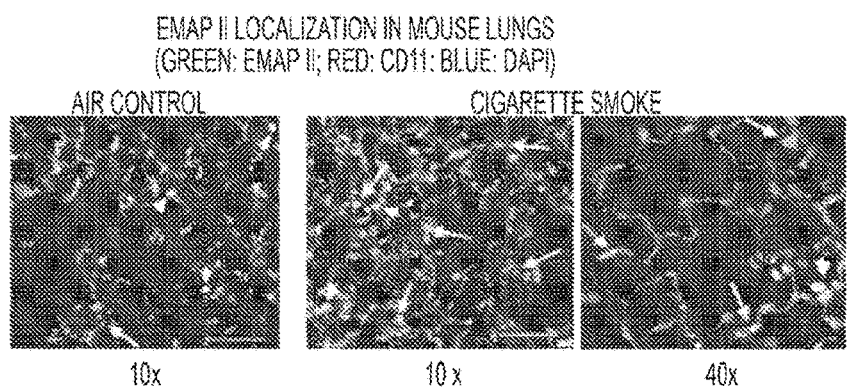
FIG. 12B. Photomicrographs of mouse lung tissue stained for EMAPII; tissue from mice exposed to CS and from exposed to ambient air (AC).

Next, the cellular localization of EMAPII expression in normal and CS-exposed mice was investigated by coimmunofluorescence with EMAPII antiserum, CD11b antibody, and DAPI. Under ambient air conditions, lungs of control mice showed sparse EMAPII expression that colocalized mostly with CD11b-labeled alveolar macrophages (FIG. 12B, left panel). By contrast, cigarette smoking robustly increased both intracellular and extracellular EMAPII production, which colocalized with both macrophages (FIG. 12B, middle panel) and alveolar septal cells (FIG. 12B, right panel).

Figure 12C:
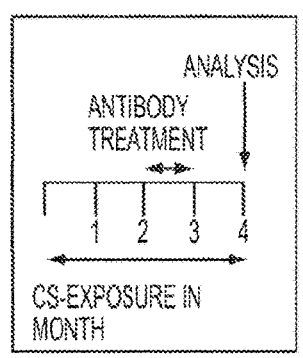
FIG. 12C. Schematic representation of treatment protocol.

The M7/1 antibody from Example 10 was used to functionally assess the role of the secreted EMAPII in CS-induced lung injury and emphysema. The M7/1 antibodies (50 μg/application) were administered directly to the lung via inhalation of a nebulized solution, which showed effective deposition in the lung parenchyma at 15 minutes by fluorescence microscopy of the lung and at 4 hours by immune adsorption analysis of recovered biotinylated antibody from plasma. This method of administration has the advantages of targeting the local EMAPII pool and has been previously shown to allow the use of lower antibody doses compared with the systemic route. The timing of M7/1 antibody delivery was chosen to follow the increases in EMAPII detected in response to CS exposure, while the duration of antibody M7/1 treatment was limited to 4 weeks to minimize or avoid nonspecific immunological side effects. DBA/2 mice were first exposed to CS alone for 8 weeks, followed by targeting EMAPII with neutralizing M7/1 antibodies between weeks 9 to 12 and 4 additional weeks of CS exposure (FIG. 12C).

Figure 12D:
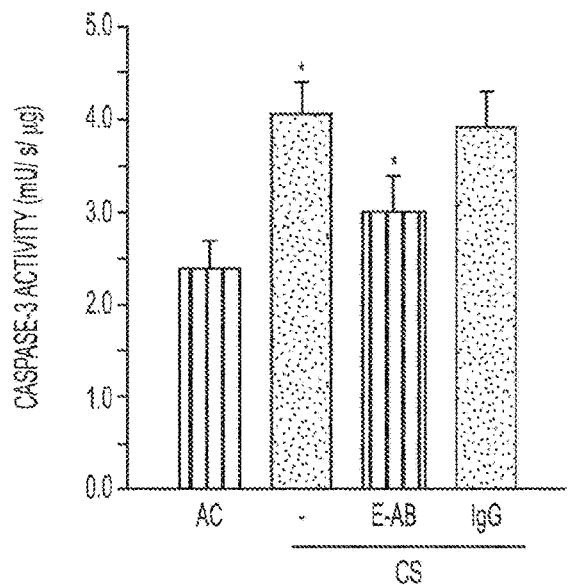
FIG. 12D. Graph showing apoptosis detected by caspase-3 activity measured in lung lysates (caspase unites normalized by protein; mean+SEM; *P<0.05, ANOVA).
Figure 12E:
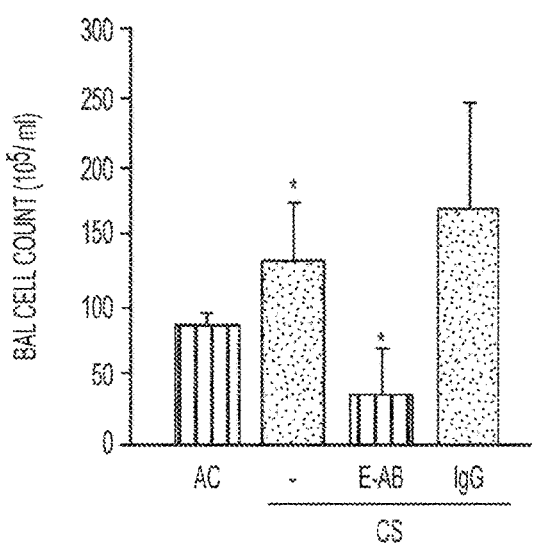
FIG. 12E. Graph showing the number of cells in BALF.
Figure 12F:
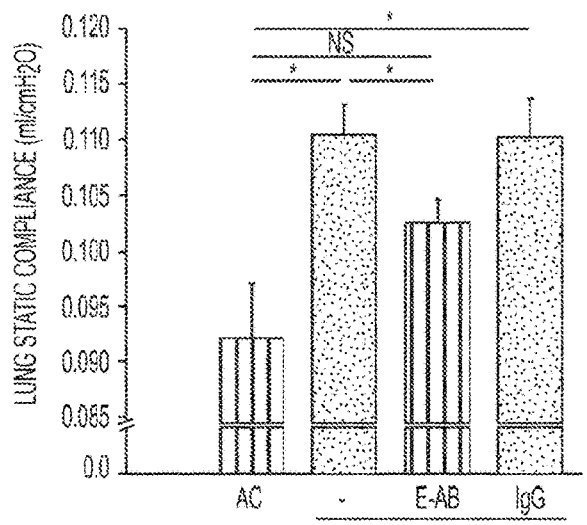
FIG. 12F. Graph showing lung static compliance (mean+ SEM; *P<0.01, ANOVA).

The administration of EMAPII-neutralizing M7/1 antibody significantly decreased lung apoptosis measured by caspase-3 activity in tissue lysates (FIG. 12D). In addition, this treatment decreased the number of inflammatory cells retrieved in the BALF (FIG. 12E), particularly alveolar macrophages and neutrophils, and reduced the number of neutrophils in the lung parenchyma. Furthermore, anti-EMAPII M7/1 antibodies significantly improved the lung static compliance (FIG. 12F) by almost 40%. Importantly, consistent with these functional data, neutralization of EMAPII abolished the CS-induced airspace enlargement measured as a 19.4% increase in MLI compared with that in air-exposed mice, which is in a typical range for CS-induced emphysema mouse models (FIGS. 2G and 2H). Interestingly, neutralizing EMAPII antibodies had no effect on CS-induced large airway epithelial remodeling but restored the thickness of the epithelial layer of small airways (smaller than 150 µm in diameter), which was significantly reduced by CS exposure. (Clauss, M. et al., Lung endothelial monocyte-activating protein 2 is a mediator of cigarette smoke-induced emphysema in mice, *J Clin Invest* doi:10.1172/JCI43881).

Example 12

Figure 5C:
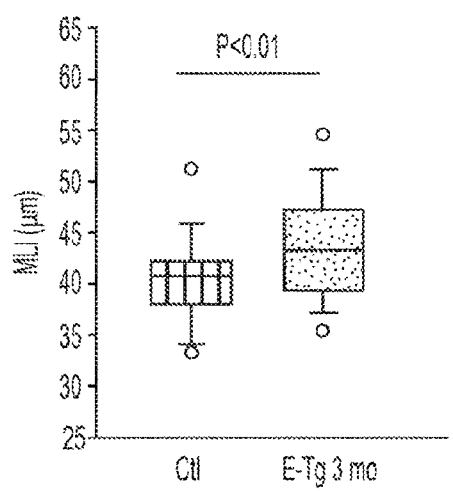
FIG. 5C. A bar graph showing the mean linear intercept of lung tissue of mice treated with tetracycline for 3 months and controls.
Figure 5E:
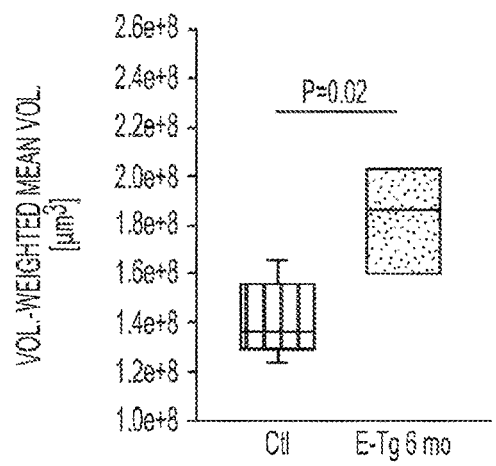
FIG. 5E. A bar graph showing the volume weighted mean volume of lung tissue of mice treated with tetracycline for 6 months and controls.
Figure 5B:
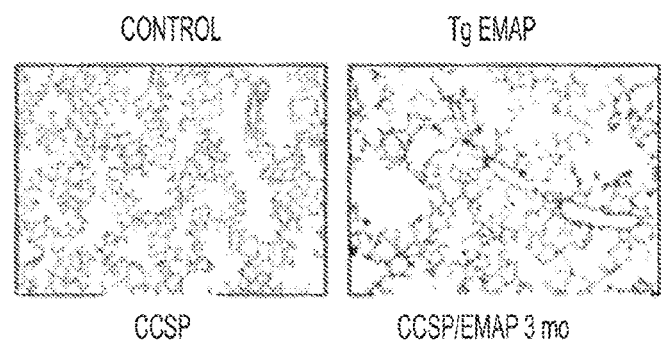
FIG. 5B. Photomicrographs of a lung section showing the alveolar after tetracycline treatment for 3 months.
Figure 5D:
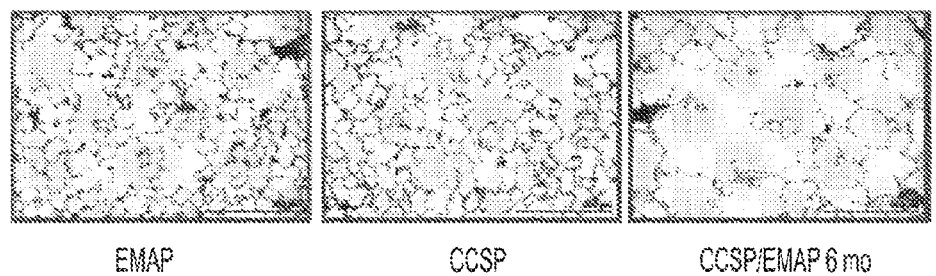
FIG. 5D. Photomicrographs of a lung section showing the alveolar after tetracycline treatment for 6 months.

Lung-Specific EMAP II Overexpression Induced Emphysema-Like Pathology of the Lung Endothelial cell death, alveolar macrophage accumulation and MMP-12 expression are implicated in emphysema pathogenesis. Lung-specific EMAP II overexpression for up to 6 months significantly increased airspace diameters, consistent with simplification of alveolar structures (FIGS. 5B-5E). The airspace enlargement was progressive, noted on hematoxyllin-eosin stained lung sections and measured by the volume-weighted mean airspace volume, which significantly increased from 1.36E+08 (±0.15, n=5) in control mice to 1.56E+08 (±0.3 SD, n=6) at 3 months (not shown) and 1.91E+08 (±0.3, n=6) at 6 months of EMAP II lung overexpression (p=0.027) (FIG. 5E). The loss of alveolar septae was further supported by an increase in the mean linear intercept in the mice overexpressing EMAP II for 3 months compared to control mice (FIG. 5C). Note that the bar in FIGS. 5B and 5D represents 300 µm. These data suggest that EMAP II increase alone may be sufficient to trigger emphysema-like airspace enlargement.

Example 13

Figure 12G:
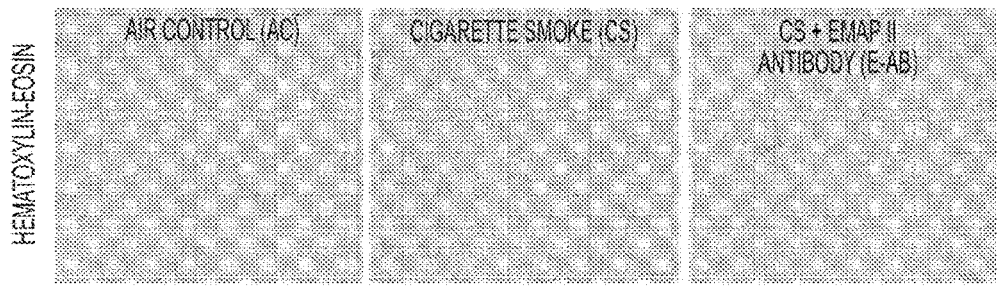
FIG. 12G. Representative H&E-stained lung sections (scale bar: 100 µm) showing simplification of lung alveolar structures in response to CS but perseved alveolar architecture when treated with neutralizing EMAPII, FIG. 12H. Morphometric measurement of MLI (mean+ SEM: *P<0.05, ANOVA: n=5-12.
Figure 12H:
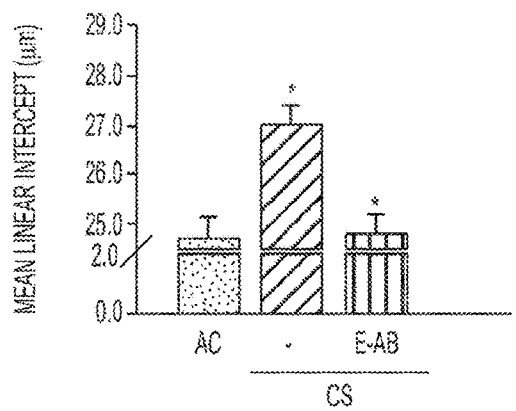

Specific Neutralization of Secreted Emap II Inhibits Cigarette Smoke-Induced Airspace Enlargement in Mice To investigate whether an excess of secreted EMAP II is also necessary for the pathogenesis of airspace enlargement in response to cigarette smoking, EMAP II was neutralized by administration of specific monoclonal antibodies in mice exposed to cigarette smoking. The DBA2 mice, which develop significant airspace enlargement after 4 months of cigarette smoke exposure, were first exposed to cigarette smoke for 2 months. For the following 1 month of exposure, specific EMAP II antibodies or isotype IgG (1 mg/kg) were administered thrice weekly via nebulization. At the end of the 4 month of total cigarette smoke exposure, lung morphometry demonstrated significant increase in airspace size consistent with simplification of alveolar structure, reminiscent of emphysema, in response to smoking but not ambient air (FIG. 12G, left panel and middle panel, bar is 100 µm). While inhaled IgG did not have an inhibitory effect on cigarette smoke-induced airspace size (not shown), treatment of mice with inhaled EMAP II antibody significantly inhibited the airspace enlargement induced by cigarette smoking (FIG. 12G, right panel, and FIG. 12H). These data suggest that application of neutralizing antibodies can reduce emphysema development even after a considerable time of smoke exposure.

Example 14

Synergistic Effects of EMAP II and Cigarette Smoke Exposure in the Lung

Having shown that EMAP II is both sufficient and necessary in smoke induced emphysema, it was next asked whether enhanced levels of baseline EMAP II in the lung sensitize the lungs to cigarette smoke-induced injury, specifically apoptosis and macrophage inflammation. Increased lung levels of EMAP II were achieved in the double transgenic mice by tetracycline administration for 8 weeks. Double transgenic (EMAP II overexpressing) or single transgenic control mice were then exposed to cigarette smoking daily, five times a week, for 4 weeks. Lungs were then assessed for levels of apoptosis by extracting and measuring whole lung apoptosis-signaling ceramides, as reported previously (Petrache, I., Natarajan, V., Zhen, L., Medler, T. R., Richter, A. T., Cho, C., Hubbard, W. C., Berdyshev, E. V., and Tuder, R. M. 2005. Ceramide upregulation causes pulmonary cell apoptosis and emphysema-like disease in mice. *Nat Med* 11:491-498). At this time point of cigarette smoke exposure, lungs of wild-type mice express only modest increases in ceramides (Petrache, I., Medler, T. R., Richter, A. T., Kamocki, K., Chukwueke, U., Zhen, L., Gu, Y., Adamowicz, J., Schweitzer, K. S., Hubbard, W. C., et al. 2008. Superoxide dismutase protects against apoptosis and alveolar enlargement induced by ceramide. *Am J Physiol Lung Cell Mol Physiol* 295:L44-53). Interestingly, there was a dramatic increase in ceramides in the lungs of mice overexpressing EMAP II prior to cigarette smoking compared to either EMAP II overexpression or cigarette smoking alone (FIG. 4A). Similarly the number of lung macrophages measured by IHC using F4/80 antibody increased synergistically in the mice overexpressing EMAP II prior to cigarette smoking compared to mice exposed for the same duration to either stimulus alone. Levels of lung ceramide (FIG. 2C), a marker of alveolar apoptosis elevated in emphysema were measured by tandem mass spectrometry and levels were normalized for lipid phosphorus (Pi) content. Horizontal lines represents median and whiskers depict the $5^{th}$ and $95^{th}$ percentile. Groups were compared by ANOVA; *p=0.01 vs control; **P=<0.006 vs. control and vs. control+cigarette smoke. H&E staining showed increased inflammatory cells in CS-exposed mice which is further aggravated in Tg mice exposed to CS. These data provide evidence for the hypothesis that EMAP II may be a predictor and mediator of emphysema formation.

Example 15

EMAP II Elevations in Human Lungs with COPD and in the Broncho-Alveolar Lavage of Smokers To investigate the relevance of increased lung EMAP II levels for human emphysema, EMAP II in subjects diagnosed with emphysema was assessed. Immunostaining (IHC) of lung samples obtained from patients with emphysema at the time of lung transplantation with specific EMAP II antibody demonstrated markedly increased EMAP II staining compared with non-diseased lungs. Interestingly, variable levels of EMAP II expression were noted in individuals without a diagnosis of COPD at the time of tissue sampling. This variability may be related to smoking status, as the BAL obtained from active smokers without a COPD diagnosis exhibited increased EMAP II levels compared to nonsmokers (FIG. 1). Secreted EMAP II (mature form) expression in the BAL acellular fluid of smokers was compared to non-smokers, as measured by Western blotting with a specific EMAP II antibody. Levels measured by densitometry of EMAP II expression in individual BAL samples. (Mean±SEM,*p=<0.01).

Example 16

Extraction of Total RNA from Hybridomas

First-round of RT-PCT. QIAGEN® OneStep RT-PCR Kit (Cat No. 210210) was used. RNA was isolation using a Qiagen kit according to standard methods in conformity with the manufacture's and the instructions. Briefly, RT-PCR was performed with primer sets specific for the heavy and light chains. For each RNA sample, 12 individual heavy chain and 11 light chain RT-PCR reactins were set up using degenerate forward primer mixtures covering the leader sequences of variable regions. Reverse primers are located in the constant regions of heavy and light chains. No restriction sites were engineered into the primers.

Second-round semi-nested PCR. The RT-PCR products from the first-round reactions were further amplified in the second-round PCR. 12 individual heavy chain and 11 light chain RT-PCR reactions were set up using sem-nested primer sets specific for antibody variable regions.

Figures 13, 14:
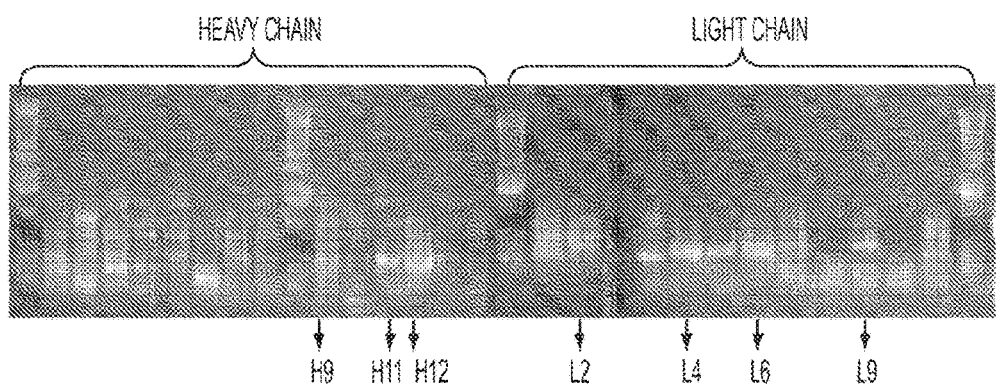
FIG. 13. Agarose gel showing PCR amplification products.
FIG. 14. Summary of results from sequences of rat antibody.

Referring now to FIG. 13. After PCR was finished, a PCR reaction was run and samples from the PCR reaction were run onto an agarose gel to visualize the DNA fragments amplified. The correct antibody variable region DNA fragments should have a size between 400-500 base pair.

Referring now to FIGS. 14 and 15. After sequencing more than 15 DNA fragments amplified by nested RT-PCR, several antibody heavy and light chains were cloned. The protein sequence and alignment and CDR analysis identified one heavy chain and one light chain Example 17

EMAP II Epitope Peptide Sequence Identification

Referring now to FIGS. 16 and 17. Based on the protocol of Parker and Tomer, tryptic digestion-derived peptides of protein bound to another compound (such as an antibody) maybe protected from digestion at the binding site. (Parker, C. et al., MALDI/MS-based epitope mapping of antigens bound to immobilized antibodies, *Molecular Biotechnology*, Volume 20, Number 1 (2002), 49-62). Accordingly, the portion of a protein bound to a sepharose-immobilized M7/1 antibody would likely be protected from proteolysis.

A binding competition was performed using human recombinant pro-EMAP II and the M7/1 antibody. Referring now to FIG. 17. Recombinant pro-EMAP II was submitted to Western blotting using control IgG and EMAP II neutralizing M7/1 antibody in the presence/absence of a 300 fold molar excess of peptide hexadecamers. Only Peptide 2 (QQSIAGSADSKPIDVSR) (SEQ. ID NO. 12) but not Peptide 1 (KHPDADSLYVEEVDVGE) (SEQ. ID NO. 13) or Peptide 3 (SEQ ID NO. 14; as a control) was able to compete with M7/1. Arrows indicate the position of molecular weight standards (in rel kDa).

Peptides in the pull-down fraction were identified by liquid chromatography tandem mass spectrometry (LC-MS/MS). By analyzing the sequences bound to protein G sepharose immobilized M7/1 antibody, protected peptides ranging over the sequence QQSIAGSADSKPIDVSRLDLRIGCIITARKHPDADSLYVEEVDVGEIAPRTVVS GLVNHVPLEQMQNRM (SEQ. ID NO. 11) were identified. From this peptide sequences 2 hexadecamer peptides randomly chosen for competition in M7/1 Western blotting: Peptide 1: KHPDADSLYVEEVDVGE (SEQ. ID NO. 13) and Peptide 2: QQSIAGSADSKPIDVSR (SEQ. ID NO. 12). A Western blotting competition assay was used in order to determine which polypeptide is the best epitope. In this assay, M7/1 antibody binding to recombinant pro-EMAP II was performed in the presence of a 300-fold excess of hexadecamer Peptides 1 or 2 or a control Peptide 3: VLKRLEQKGAEADQIIE (SEQ. ID NO. 14). Peptide 2 competed strongly for the M7/1 antibody binding as indicated by the absence of a Western blot band for M7/1 staining, whereas the other identified Peptide 1 and the control Peptide 3 had no effect.

It should be understood, of course, that the foregoing relates to exemplary embodiments of the invention and that modifications may be made without departing from the spirit and scope of the invention as set forth in the following claims.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

We claim:

1. A method of making an antibody, the method comprising the steps of:
   contacting the immune system of a mammal with a polypeptide consisting of SEQ ID NO: 12; and
   selecting a B-cell from the mammal;
   wherein the B-cell produces antibodies that bind to endothelial monocyte activating protein II (EMAP II).

2. The method according to claim 1, wherein contacting the immune system of the mammal comprises immunizing the mammal.

3. The method according to claim 1, wherein selecting a B-cell from the mammal comprises isolating B-cells from the mammal, fusing the B-cells with myeloma cells thereby forming hybridomas, and selecting at least one hybridoma.

4. The method according to claim 3, wherein the at least one hybridoma is selected by testing hybridoma supernatant for binding of EMAP II by enzyme linked immunosuppression assay (ELISA).

* * * * *

SEQUENCE LISTING

```
<160> NUMBER OF SEQ ID NOS: 15

<210> SEQ ID NO 1
<211> LENGTH: 354
<212> TYPE: DNA
<213> ORGANISM: Rattus rattus

<400> SEQUENCE: 1
```

```
gcggtgcacc ttgttgagtc tggtggagga tttgtgcagc ctacggagtc attgaaaatc      60
tcatgtgcag cctctggatt caccttcagt gatgctgcca tgtactgggt ccgccaggct     120
ccaggaaagg gtctggaatg ggttgctcgc ataagaacta aacctaataa ttatgcaaca     180
tattatgctg attcagtgaa aggcagattc accatctccc gagatgattc aaaaagcatg     240
gtctacctac aaatggataa cttgaaaact gaggacacag ccatgtatta ctgtacatca     300
tggagctacg actttgatta ctggggccaa ggagtcatgg tcacagtctc ctca           354
```

\<210\> SEQ ID NO 2
\<211\> LENGTH: 118
\<212\> TYPE: PRT
\<213\> ORGANISM: Rattus rattus

\<400\> SEQUENCE: 2

```
Ala Val His Leu Val Glu Ser Gly Gly Gly Phe Val Gln Pro Thr Glu
1               5                   10                  15

Ser Leu Lys Ile Ser Cys Ala Ala Ser Gly Phe Thr Phe Ser Asp Ala
            20                  25                  30

Ala Met Tyr Trp Val Arg Gln Ala Pro Gly Lys Gly Leu Glu Trp Val
        35                  40                  45

Ala Arg Ile Arg Thr Lys Pro Asn Asn Tyr Ala Thr Tyr Tyr Ala Asp
    50                  55                  60

Ser Val Lys Gly Arg Phe Thr Ile Ser Arg Asp Asp Ser Lys Ser Met
65                  70                  75                  80

Val Tyr Leu Gln Met Asp Asn Leu Lys Thr Glu Asp Thr Ala Met Tyr
                85                  90                  95

Tyr Cys Thr Ser Trp Ser Tyr Asp Phe Asp Tyr Trp Gly Gln Gly Val
            100                 105                 110

Met Val Thr Val Ser Ser
        115
```

\<210\> SEQ ID NO 3
\<211\> LENGTH: 112
\<212\> TYPE: PRT
\<213\> ORGANISM: Rattus rattus

\<400\> SEQUENCE: 3

```
Asp Ile Val Met Thr Gln Gly Ala Leu Pro Asn Pro Val Pro Ser Gly
1               5                   10                  15

Glu Ser Ala Ser Ile Thr Cys Gln Ser Ser Lys Ser Leu Leu His Ser
            20                  25                  30

Ser Gly Lys Thr Tyr Leu Asn Trp Tyr Leu Gln Arg Pro Gly Gln Ser
        35                  40                  45

Pro His Leu Leu Ile Tyr Trp Met Ser Thr Arg Ala Ser Gly Val Ser
    50                  55                  60

Asp Arg Leu Ser Gly Ser Gly Ser Gly Thr Asp Phe Thr Leu Lys Ile
65                  70                  75                  80

Ser Ser Val Glu Ala Glu Asp Val Gly Val Tyr Tyr Cys Gln Gln Phe
                85                  90                  95

Leu Glu Tyr Pro Leu Thr Phe Gly Ser Gly Thr Lys Leu Glu Ile Lys
            100                 105                 110
```

\<210\> SEQ ID NO 4
\<211\> LENGTH: 337
\<212\> TYPE: DNA
\<213\> ORGANISM: Rattus rattus

<400> SEQUENCE: 4

```
gatattgtga tgacccaggg tgcactcccc aaccctgtcc cctctggaga gtcagcttcc      60
atcacctgcc agtctagtaa gagtctgctg cacagcagtg gcaagacata cttgaattgg    120
tatctgcaga ggccaggaca gtctcctcat ctcctgatct attggatgtc cacccgtgca    180
tcaggagtct cagacaggct cagtggcagt gggtcaggaa cagatttcac actgaaaatc    240
agcagcgtgg aggctgagga tgtgggtgtg tattactgtc agcaatttct agagtatcct    300
ctcacgttcg gttctgggac caagctggag atcaaac                             337
```

<210> SEQ ID NO 5
<211> LENGTH: 8
<212> TYPE: PRT
<213> ORGANISM: Rattus rattus

<400> SEQUENCE: 5

Gly Phe Thr Phe Ser Asp Ala Ala
1               5

<210> SEQ ID NO 6
<211> LENGTH: 10
<212> TYPE: PRT
<213> ORGANISM: Rattus rattus

<400> SEQUENCE: 6

Ile Arg Thr Lys Pro Asn Asn Tyr Ala Thr
1               5                   10

<210> SEQ ID NO 7
<211> LENGTH: 9
<212> TYPE: PRT
<213> ORGANISM: Rattus rattus

<400> SEQUENCE: 7

Thr Ser Trp Ser Tyr Asp Phe Asp Tyr
1               5

<210> SEQ ID NO 8
<211> LENGTH: 11
<212> TYPE: PRT
<213> ORGANISM: Rattus rattus

<400> SEQUENCE: 8

Lys Ser Leu Leu His Ser Ser Gly Lys Thr Tyr
1               5                   10

<210> SEQ ID NO 9
<211> LENGTH: 3
<212> TYPE: PRT
<213> ORGANISM: Rattus rattus

<400> SEQUENCE: 9

Trp Met Ser
1

<210> SEQ ID NO 10
<211> LENGTH: 9
<212> TYPE: PRT
<213> ORGANISM: Rattus rattus

<400> SEQUENCE: 10

Gln Gln Phe Leu Glu Tyr Pro Leu Thr

```
<210> SEQ ID NO 11
<211> LENGTH: 69
<212> TYPE: PRT
<213> ORGANISM: Homo sapiens

<400> SEQUENCE: 11

Gln Gln Ser Ile Ala Gly Ser Ala Asp Ser Lys Pro Ile Asp Val Ser
1               5                   10                  15

Arg Leu Asp Leu Arg Ile Gly Cys Ile Ile Thr Ala Arg Lys His Pro
            20                  25                  30

Asp Ala Asp Ser Leu Tyr Val Glu Val Asp Val Gly Glu Ile Ala
        35                  40                  45

Pro Arg Thr Val Val Ser Gly Leu Val Asn His Val Pro Leu Glu Gln
    50                  55                  60

Met Gln Asn Arg Met
65

<210> SEQ ID NO 12
<211> LENGTH: 17
<212> TYPE: PRT
<213> ORGANISM: Homo sapiens

<400> SEQUENCE: 12

Gln Gln Ser Ile Ala Gly Ser Ala Asp Ser Lys Pro Ile Asp Val Ser
1               5                   10                  15

Arg

<210> SEQ ID NO 13
<211> LENGTH: 17
<212> TYPE: PRT
<213> ORGANISM: Homo sapiens

<400> SEQUENCE: 13

Lys His Pro Asp Ala Asp Ser Leu Tyr Val Glu Val Asp Val Gly
1               5                   10                  15

Glu

<210> SEQ ID NO 14
<211> LENGTH: 17
<212> TYPE: PRT
<213> ORGANISM: Artificial Sequence
<220> FEATURE:
<223> OTHER INFORMATION: synthetic

<400> SEQUENCE: 14

Val Leu Lys Arg Leu Glu Gln Lys Gly Ala Glu Ala Asp Gln Ile Ile
1               5                   10                  15

Glu

<210> SEQ ID NO 15
<211> LENGTH: 672
<212> TYPE: PRT
<213> ORGANISM: Homo sapiens

<400> SEQUENCE: 15

Met Leu Pro Ala Val Ala Val Ser Glu Pro Val Val Leu Arg Phe Met
1               5                   10                  15

Ile Phe Cys Arg Leu Leu Ala Lys Met Ala Asn Asn Asp Ala Val Leu
            20                  25                  30
```

-continued

```
Lys Arg Leu Glu Gln Lys Gly Ala Glu Ala Asp Gln Ile Ile Glu Tyr
             35                  40                  45
Leu Lys Gln Gln Val Ser Leu Leu Lys Glu Lys Ala Ile Leu Gln Ala
 50                  55                  60
Thr Leu Arg Glu Glu Lys Lys Leu Arg Val Glu Asn Ala Lys Leu Lys
 65                  70                  75                  80
Lys Glu Ile Glu Glu Leu Lys Gln Glu Leu Ile Gln Ala Glu Ile Gln
                     85                  90                  95
Asn Gly Val Lys Gln Ile Pro Phe Pro Ser Gly Thr Pro Leu His Ala
                 100                 105                 110
Asn Ser Met Val Ser Glu Asn Val Ile Gln Ser Thr Ala Val Thr Thr
             115                 120                 125
Val Ser Ser Gly Thr Lys Glu Gln Ile Lys Gly Gly Thr Gly Asp Glu
 130                 135                 140
Lys Lys Ala Lys Glu Lys Ile Glu Lys Lys Gly Glu Lys Lys Glu Lys
145                 150                 155                 160
Lys Gln Gln Ser Ile Ala Gly Ser Ala Asp Ser Lys Pro Ile Asp Val
                 165                 170                 175
Ser Arg Leu Asp Leu Arg Ile Gly Cys Ile Ile Thr Ala Arg Lys His
             180                 185                 190
Pro Asp Ala Asp Ser Leu Tyr Val Glu Glu Val Asp Val Gly Glu Ile
             195                 200                 205
Ala Pro Arg Thr Val Val Ser Gly Leu Val Asn His Val Pro Leu Glu
 210                 215                 220
Gln Met Gln Asn Arg Met Val Ile Leu Leu Cys Asn Leu Lys Pro Ala
225                 230                 235                 240
Lys Met Arg Gly Val Leu Ser Gln Ala Met Val Met Cys Ala Ser Ser
                 245                 250                 255
Pro Glu Lys Ile Glu Ile Leu Ala Pro Pro Asn Gly Ser Val Pro Gly
             260                 265                 270
Asp Arg Ile Thr Phe Asp Ala Phe Pro Gly Glu Pro Asp Lys Glu Leu
             275                 280                 285
Asn Pro Lys Lys Lys Ile Trp Glu Gln Ile Gln Pro Asp Leu His Thr
 290                 295                 300
Asn Asp Glu Cys Val Ala Thr Tyr Lys Gly Val Pro Phe Glu Val Lys
305                 310                 315                 320
Gly Lys Gly Val Cys Arg Ala Gln Thr Met Ser Asn Ser Gly Ile Lys
                 325                 330                 335
Met Leu Pro Ala Val Ala Val Ser Glu Pro Val Val Leu Arg Phe Met
             340                 345                 350
Ile Phe Cys Arg Leu Leu Ala Lys Met Ala Asn Asn Asp Ala Val Leu
             355                 360                 365
Lys Arg Leu Glu Gln Lys Gly Ala Glu Ala Asp Gln Ile Ile Glu Tyr
 370                 375                 380
Leu Lys Gln Gln Val Ser Leu Leu Lys Glu Lys Ala Ile Leu Gln Ala
385                 390                 395                 400
Thr Leu Arg Glu Glu Lys Lys Leu Arg Val Glu Asn Ala Lys Leu Lys
                 405                 410                 415
Lys Glu Ile Glu Glu Leu Lys Gln Glu Leu Ile Gln Ala Glu Ile Gln
             420                 425                 430
Asn Gly Val Lys Gln Ile Pro Phe Pro Ser Gly Thr Pro Leu His Ala
             435                 440                 445
```

-continued

```
Asn Ser Met Val Ser Glu Asn Val Ile Gln Ser Thr Ala Val Thr Thr
    450             455                 460
Val Ser Ser Gly Thr Lys Glu Gln Ile Lys Gly Gly Thr Gly Asp Glu
465             470                 475                 480
Lys Lys Ala Lys Glu Lys Ile Glu Lys Lys Gly Glu Lys Lys Glu Lys
                485                 490                 495
Lys Gln Gln Ser Ile Ala Gly Ser Ala Asp Ser Lys Pro Ile Asp Val
            500                 505                 510
Ser Arg Leu Asp Leu Arg Ile Gly Cys Ile Ile Thr Ala Arg Lys His
            515                 520                 525
Pro Asp Ala Asp Ser Leu Tyr Val Glu Val Asp Val Gly Glu Ile
530                 535                 540
Ala Pro Arg Thr Val Val Ser Gly Leu Val Asn His Val Pro Leu Glu
545                 550                 555                 560
Gln Met Gln Asn Arg Met Val Ile Leu Leu Cys Asn Leu Lys Pro Ala
                565                 570                 575
Lys Met Arg Gly Val Leu Ser Gln Ala Met Val Met Cys Ala Ser Ser
            580                 585                 590
Pro Glu Lys Ile Glu Ile Leu Ala Pro Pro Asn Gly Ser Val Pro Gly
            595                 600                 605
Asp Arg Ile Thr Phe Asp Ala Phe Pro Gly Glu Pro Asp Lys Glu Leu
        610                 615                 620
Asn Pro Lys Lys Lys Ile Trp Glu Gln Ile Gln Pro Asp Leu His Thr
625                 630                 635                 640
Asn Asp Glu Cys Val Ala Thr Tyr Lys Gly Val Pro Phe Glu Val Lys
                645                 650                 655
Gly Lys Gly Val Cys Arg Ala Gln Thr Met Ser Asn Ser Gly Ile Lys
                660                 665                 670
```